United States Patent [19]
Granger et al.

[11] Patent Number: 5,858,699
[45] Date of Patent: Jan. 12, 1999

[54] METHOD TO STABILIZE CELL SUSPENSIONS USING AGED HEAVY METAL SOLUTION AND PARAFORMALDEHYDE

[75] Inventors: Vivian Granger; David Barnett, both of Sheffield, United Kingdom

[73] Assignee: Northern General Hospital NHS Trust, United Kingdom

[21] Appl. No.: 718,359

[22] PCT Filed: Apr. 5, 1995

[86] PCT No.: PCT/EP95/01259

§ 371 Date: Jan. 27, 1997

§ 102(e) Date: Jan. 27, 1997

[87] PCT Pub. No.: WO95/27203

PCT Pub. Date: Oct. 12, 1995

[30] Foreign Application Priority Data

Apr. 5, 1994 [GB] United Kingdom .................. 9406698
Jul. 4, 1994 [GB] United Kingdom .................. 9413558

[51] Int. Cl.$^6$ ........................................... C12Q 1/08
[52] U.S. Cl. ................................. 435/40.51; 435/40.51; 436/10; 436/17
[58] Field of Search .................. 436/10, 17; 435/2, 435/40.51, 40.5

[56] References Cited

U.S. PATENT DOCUMENTS

| | | |
|---|---|---|
| 4,045,488 | 8/1977 | Sarges . |
| 4,123,384 | 10/1978 | Hundt et al. .............. 252/408 |
| 4,152,208 | 5/1979 | Guirgis . |
| 4,324,687 | 4/1982 | Louderback . |
| 4,704,352 | 11/1987 | Miripol et al. ............... 435/2 |
| 4,806,343 | 2/1989 | Carpenter . |
| 4,833,090 | 5/1989 | Liss . |
| 5,270,208 | 12/1993 | Ryan . |
| 5,422,277 | 6/1995 | Connelly et al. ............ 436/10 |

FOREIGN PATENT DOCUMENTS

| | | |
|---|---|---|
| 0030710 | 12/1980 | European Pat. Off. . |
| 1147004 | 4/1963 | Germany . |
| 5164758 | 6/1993 | Japan . |
| 1767436 | 5/1990 | U.S.S.R. . |
| 0901675 | 7/1962 | United Kingdom . |
| 1302564 | 1/1973 | United Kingdom . |
| 1449228 | 9/1976 | United Kingdom . |
| 2001757 | 2/1979 | United Kingdom . |
| 1563839 | 4/1980 | United Kingdom . |
| 1583320 | 1/1981 | United Kingdom . |
| 2077916 | 12/1981 | United Kingdom . |
| 2099281 | 12/1982 | United Kingdom . |
| 2279653 | 1/1995 | United Kingdom . |
| 8703484 | 6/1987 | WIPO . |
| 8705113 | 8/1987 | WIPO . |
| 9117436 | 11/1991 | WIPO . |
| 9219951 | 11/1992 | WIPO . |
| 9321928 | 11/1993 | WIPO . |
| 9407532 | 4/1994 | WIPO . |
| 9501796 | 1/1995 | WIPO . |
| 9527203 | 10/1995 | WIPO . |

OTHER PUBLICATIONS

Cornelis, R. et al., "Chromium Speciation Studies in Human Plasma and Stability Studies of Cr (III) and CR (VI) Species in a Candidate Water Reference Material"; *Mikrochim.Acta* 109: 145–148 (1992).

*Primary Examiner*—Sandra E. Saucier
*Attorney, Agent, or Firm*—Sheldon & Mak

[57] ABSTRACT

A stabilized cell suspension is prepared by treating the cell suspension with a solution of a heavy metal compound, which has been aged at pH 6.5–7.5 prior to use to allow a precipitate to form, removing the precipitate from the heavy metal solution, mixing the aged heavy metal solution with the cell suspension to form a first mixture, and mixing the first mixture with a paraformaldehyde solution to form a stabilized cell suspension which is still capable of lysis.

23 Claims, 27 Drawing Sheets

| QUAD | CELL TYPE | CORR % L | CELLS/ cu mm |
|---|---|---|---|
| 1 | CD4+/CD3- | 2 | 30 |
| 2 | CD3+/CD4+ | 18 | 310 |
| 3 | NEGATIVE | 8 | 140 |
| 4 | CD3+/CD4- | 71 | 1210 |

GATED EVENTS: 2396
TOTAL EVENTS: 10000

| QUAD | CELL TYPE | CORR % L | CELLS/ cu mm |
|---|---|---|---|
| 1 | CD8+/CD3- | 3 | 50 |
| 2 | CD8+/CD3+ | 71 | 1210 |
| 3 | NEGATIVE | 7 | 120 |
| 4 | CD8-/CD3+ | 19 | 320 |

GATED EVENTS: 3646
TOTAL EVENTS: 15000

GATED EVENTS: 2409
TOTAL EVENTS: 15000

GATED EVENTS: 3149
TOTAL EVENTS: 15000

GATED EVENTS: 7289
TOTAL EVENTS: 50000

FIG.3a(ii)
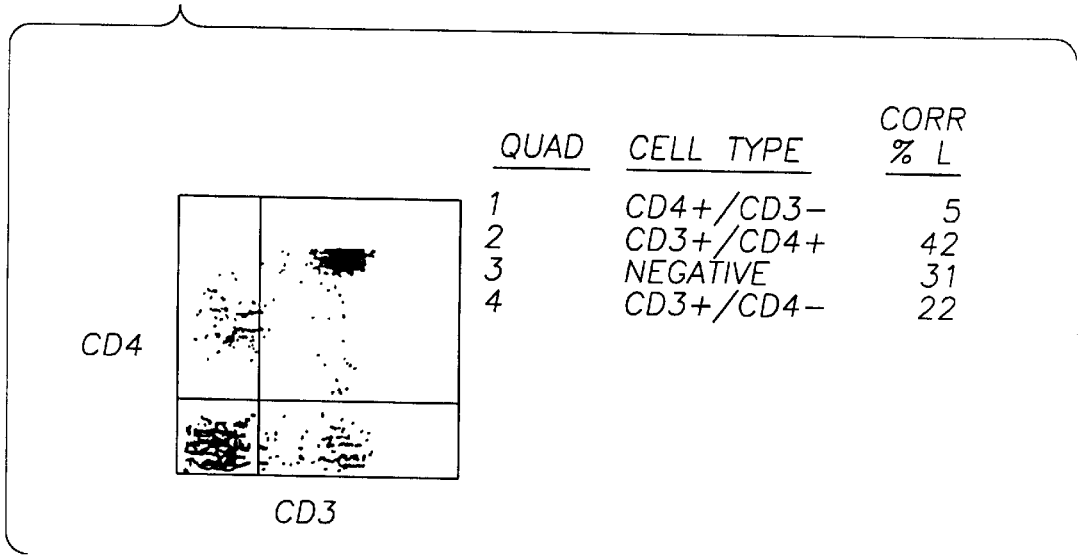
FIG.3b(ii)
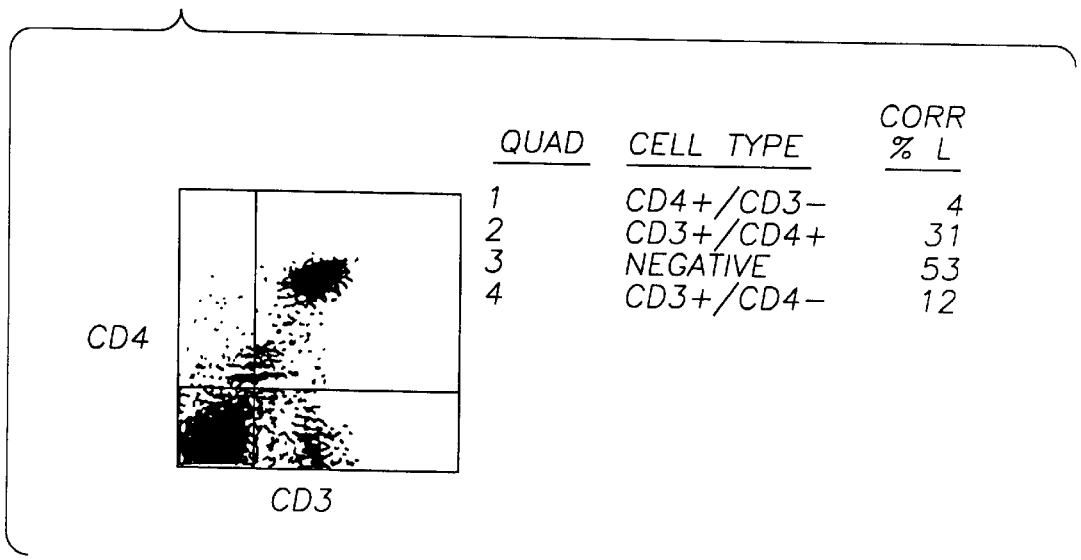

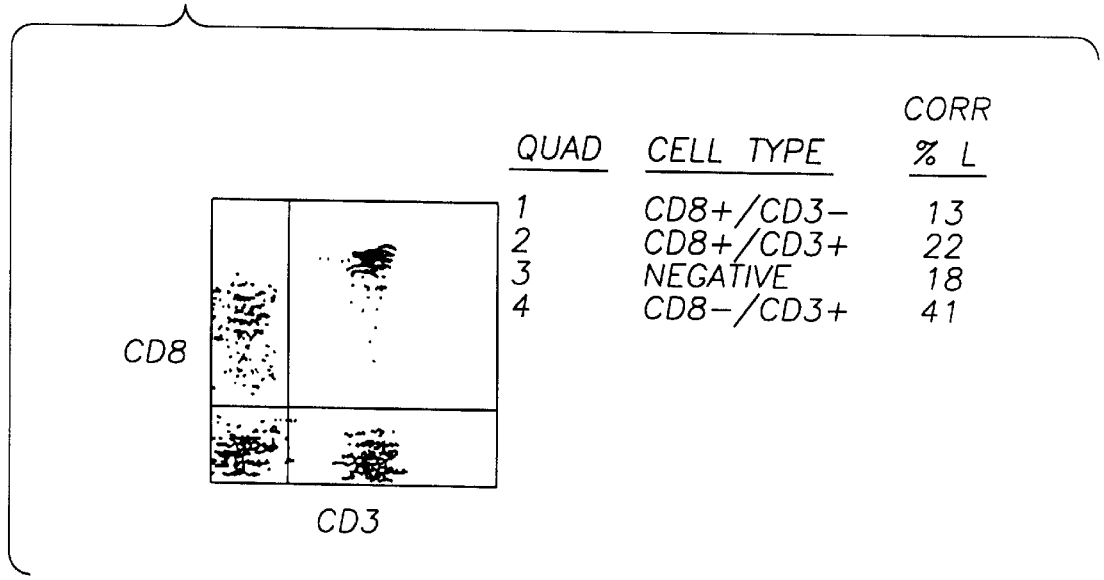
FIG.3a(iii)
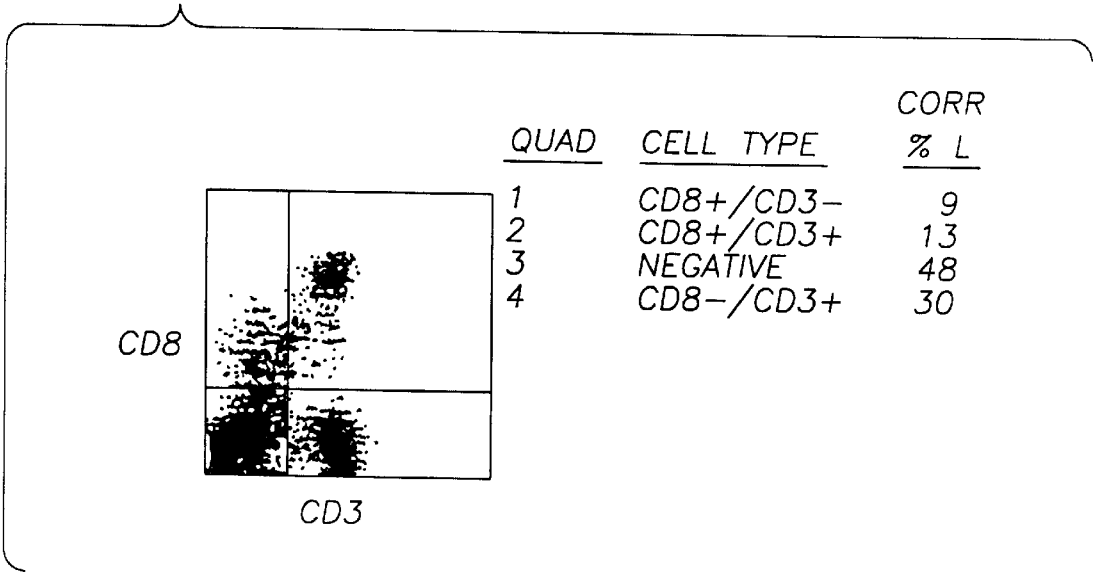
FIG.3b(iii)

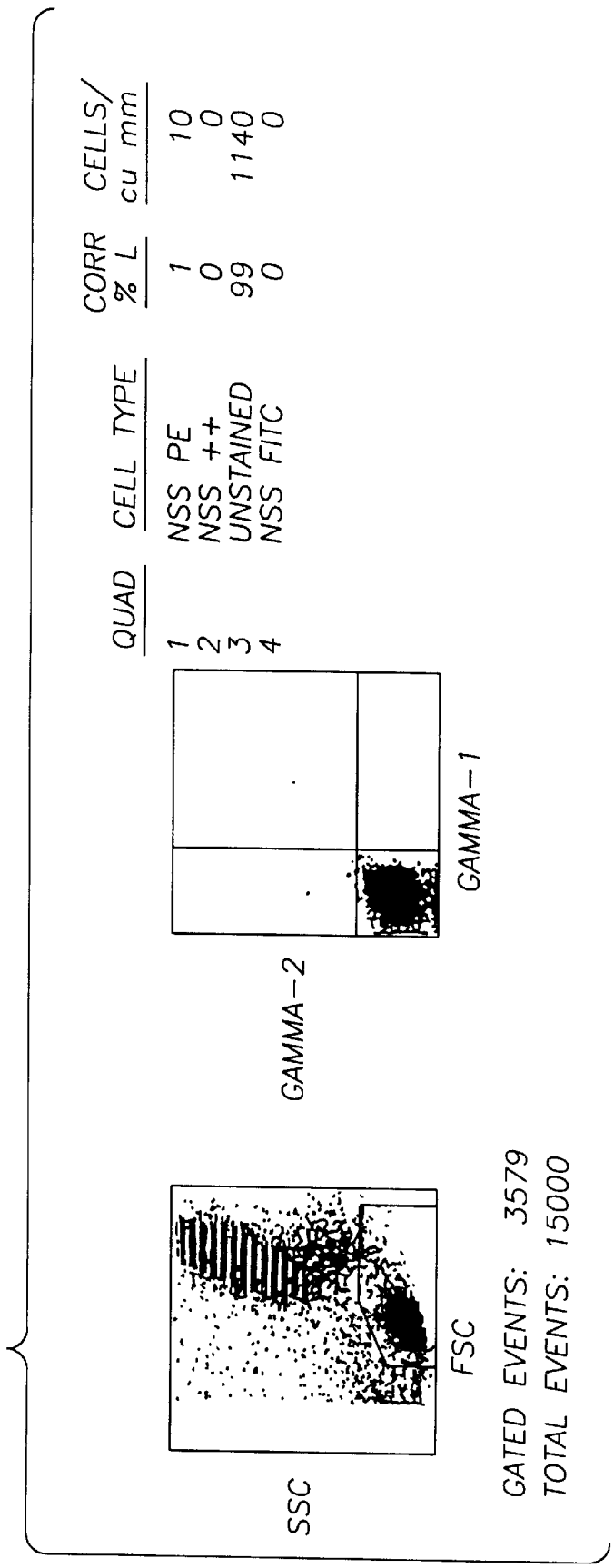

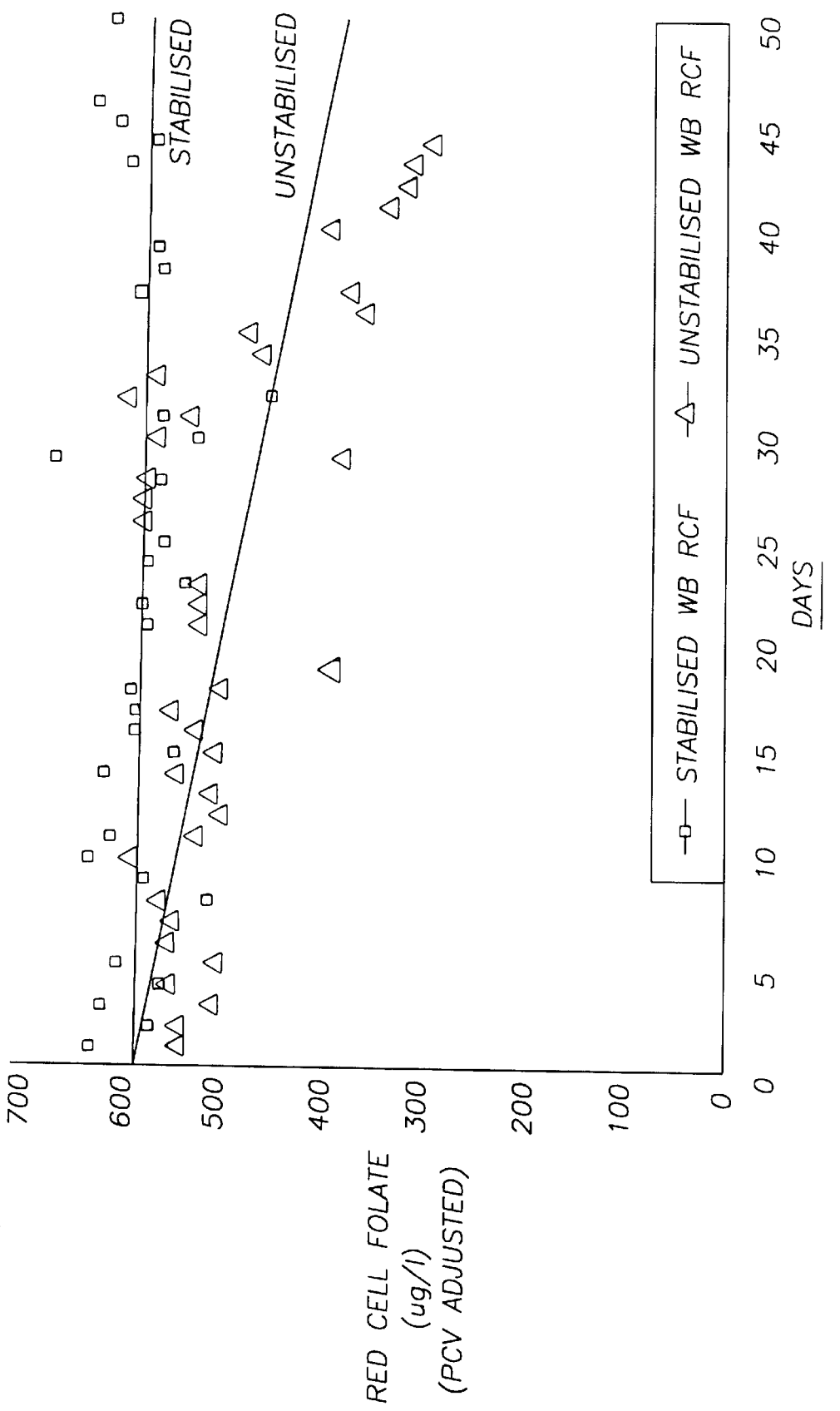

FIG.12a

| QUAD | CELL TYPE | CORR % L | CELLS/ cu mm |
|---|---|---|---|
| 1 | CD3-/CD19+ | 5 | 70 |
| 2 | CD3+/CD19+ | 0 | 0 |
| 3 | CD3-/CD19- | 13 | 190 |
| 4 | CD3+/CD19- | 82 | 1210 |

| SUBSET LABEL | | CORR % L |
|---|---|---|
| Q1 | CD3/CD19 | 5 OK |
| Q2 | CD3/CD19 | 0 OK |
| Q3 | CD3/CD19 | 13 OK |
| Q4 | CD3/CD19 | 82 OK |

(Axes: CD19 vs CD3)

FIG.12b

| QUAD | CELL TYPE | CORR % L | CELLS/ cu mm |
|---|---|---|---|
| 1 | CD3-/CD4+ | 3 | 40 |
| 2 | CD3+/CD4+ | 44 | 650 |
| 3 | CD3-/CD4- | 14 | 210 |
| 4 | CD3+/CD4- | 39 | 580 |

| SUBSET LABEL | | CORR % L |
|---|---|---|
| Q1 | CD3/CD4 | 3 OK |
| Q2 | CD3/CD4 | 44 OK |
| Q3 | CD3/CD4 | 14 OK |
| Q4 | CD3/CD4 | 39 OK |

(Axes: CD4 vs CD3)

| QUAD | CELL TYPE | CORR % L | CELLS/ cu mm |
|------|-----------|----------|--------------|
| 1 | CD3−/CD19+ | 4 | 70 |
| 2 | CD3+/CD19+ | 0 | 0 |
| 3 | CD3−/CD19− | 14 | 230 |
| 4 | CD3+/CD19− | 82 | 1340 |

| | SUBSET | LABEL | CORR % L | |
|--|--------|-------|----------|--|
| Q1 | CD3/CD19 | | 4 | OK |
| Q2 | CD3/CD19 | | 0 | OK |
| Q3 | CD3/CD19 | | 14 | OK |
| Q4 | CD3/CD19 | | 82 | OK |

GATED EVENTS:  2430
TOTAL EVENTS: 10000

| QUAD | CELL TYPE | CORR % L | CELLS/ cu mm |
|------|-----------|----------|--------------|
| 1 | CD3−/CD4+ | 3 | 50 |
| 2 | CD3+/CD4+ | 43 | 710 |
| 3 | CD3−/CD4− | 14 | 230 |
| 4 | CD3+/CD4− | 40 | 660 |

| | SUBSET | LABEL | CORR % L | |
|--|--------|-------|----------|--|
| Q1 | CD3/CD4 | | 3 | OK |
| Q2 | CD3/CD4 | | 43 | OK |
| Q3 | CD3/CD4 | | 14 | OK |
| Q4 | CD3/CD4 | | 40 | OK |

GATED EVENTS:  2359
TOTAL EVENTS: 10000

METHOD TO STABILIZE CELL SUSPENSIONS USING AGED HEAVY METAL SOLUTION AND PARAFORMALDEHYDE

BACKGROUND OF THE INVENTION

This invention relates to the preparation and stabilisation of cell suspensions, and more particularly to a novel method for preparing and stabilising cell suspensions, and to the use of novel stabilised cell suspension preparations in the quality control of analytical techniques such as UV microscopy and flow cytometric leucocyte immunophenotyping techniques, immobilised antigen/antibody detection systems and haematology analysers, and blood monitoring techniques such as zinc protoporphyrin (ZPP), red cell folate and blood glucose measurements.

UV microscopy and flow cytometry are techniques used in the diagnosis of haematological malignancies. They are also used to monitor the progress of patients infected with the Human Immunodeficiency Virus (HIV) whether asymptomatic or suffering from ARC or full-blown AIDS. Quality control (QC) of these two techniques is extremely important to arrive at the correct diagnosis and to monitor effective therapeutic regimes. The current QC methods use freshly drawn blood or microspheres coated with a fluorochrome.

The use of fresh blood on a daily basis fails to provide the information on day to day variation of the technique or equipment. Furthermore, fluorochrome coated microspheres, though providing a day to day monitor of the flow cytometer's performance cannot be used for UV microscopy work. In addition, they cannot be used to provide quality control for the labelling techniques of leucocytes.

Fixation of normal leucocytes, utilising compounds such as paraformaldehyde, although giving stability for 5–7 days increases cellular autofluorescence. This makes the preparation unsuitable for use as a long term quality control material. Furthermore, the lysis of red calls by the whole blood lysing technique requires a preparation that will quality control this procedure. The current methods of fixing the leucocytes inhibit this lysing procedure resulting in a significant increase in debris that interferes with the tests.

Other QC equipment requiring the use of whole blood samples or blood products for calibration include haematology analysers where currently fixed blood from donkeys and turkeys is used because a suitable source of stabilised human blood is not available. Zinc protoporphyrin (ZPP) and red cell folate monitoring techniques also require a fresh suspension of red blood cells for calibration, again because a suitable stabilised source is not available. Finally the lack of a stabilised source of whole human blood for calibration purposes limits the possibility for diabetics to carry out blood sugar monitoring at home.

In International Application No. WO 91/17436, the entire disclosure of which is incorporated herein by reference, there is described a blood diluent and lysing agent for differential determination of white blood cells (leucocytes) in which the stabilising agent is diazolidinyl urea. Such leucocyte preparations have not been suggested as flow cytometric preparations possibly because they have insufficient stability and lack certain specific antigenic activity for those routine quality control procedures which need to assess-results from a large number of laboratories.

International Application No. WO92/19951 discloses the use of diazolidinyl urea, imidazolidinyl urea, dimethylol-5, 5-dimethylhydantoin, dimethylol urea, 2-bromo-2-nitropropane-1,3-diol and quaternary adamantane as tissue fixatives which are free of aldehydes. The formulations may contain inter alia mordants such as zinc, calcium, barium and chromium salts. It is not suggested, however, that any of these salts have stabilising properties.

G81563839 provides a process for preparing a stabilised preparation of erythrocytes, wherein a suspension of erythrocytes in an aqueous isotonic solution is reacted with, simultaneously or successively in any sequence, an aliphatic aldehyde and a water-soluble salt of 2- or 3- valent chromium. In the examples, the erythrocytes are treated with formaldehyde and glutaraldehyde, followed by an aqueous solution of chromium III chloride.

It has been found that cell suspensions containing erythrocytes treated in this way are no longer suitable for use in a whole blood lysing technique, and thus the process of GB1563839 cannot be used to prepare stabilised whole blood samples, for example, for flow cytometry quality control.

GB2001757 describes a method of preparing a stable suspension of blood platelets which comprises adding chromium ions to a platelet-rich plasma and adding at least one organic aldehyde to the chromium-platelet-rich plasma mixture. In the examples, the platelet-rich plasma is treated with solutions of potassium dichromate and glutaraldehyde. This process, if used on leucocyte cells, substantially increases autofluorescence and renders the suspension unsuitable for use in flow cytometry.

The entire disclosures of the above-mentioned patent and applications are incorporated herein by reference.

It will be appreciated from the above, that there is a need for an improved method for stabilising cell suspensions, particularly of whole blood and blood products, giving a cell preparation that is still capable of lysis, for a variety of quality control, monitoring and calibration applications.

In UK Patent Application No. GB2279653 it is disclosed that certain heavy metal compounds can stabilise leucocyte preparations formed from lysed whole blood, and that such stabilised preparations can be added to leucocyte-deplated blood to provide a stabilized whole blood preparation with high antigenic activity. The entire disclosures of these applications are incorporated herein by reference.

OBJECTS OF THE INVENTION

It is an object of the invention to provide an improved stabilised cell suspension preparation which is still capable of lysis and an improved method for producing such stabilised cell suspensions.

It is also an object of the invention to provide a stabilised whole blood preparation which is still capable of lysts and a method of manufacturing such a preparation.

It is a still further object of the invention to provide stable quality control materials which can be used in a wide spectrum of quality control, analysis and monitoring techniques.

SUMMARY OF THE INVENTION

It has now been discovered that a wide range of cell suspensions comprising cells capable of lysis can be stabilised by the sequential addition of a heavy metal compound and paraformaldehyde to the suspension in effective amounts, and that such stabilised cell suspensions will remain active for much longer periods then those known hitherto.

In one aspect the invention provides a method of treating a suspension of Tells capable of lysis, to produced a stabilised cell suspension still capable of lysis, which comprises:

treating the cell suspension, in an aqueous medium maintained at a pH of from 6.5 to 7.5, sequentially with,
1) an aged aqueous solution of a heavy metal compound, the pH of the solution being from 6.5 to 7.5, and the solution having been maintained at a pH of from 6.5 to 7.5 for a period of time sufficient to allow any precipitate to form, and
2) an aqueous solution of paraformaldehyde, the pH of the solution being from 6.5 to 7.5.

The invention is particularly applicable to the stabilisation of whole blood and of blood products and will be henceforth more particularly described with reference thereto. It is to be understood, however that the invention is not limited to the stabilisation of such materials, and is broadly applicable to a wide range of cell suspension capable of lysis.

In a further aspect, therefore, the invention provides an unseparated stabilised whole blood preparation capable of lysis in which the stabilizing agent comprises effective amounts of a heavy metal compound, particularly a heavy metal salt, and paraformaldehyde, and a method of stabilising a whole blood preparation capable of lysis by adding effective amounts of the compound and paraformaldehyde thereto.

BRIEF DESCRIPTION OF THE DRAWINGS

FIGS. 4a and 4b show the stability of FSC, SSC and the negative control characteristics, as determined by flow cytometry, upon the stabilised whole blood preparation, over a 60 day period;

FIG. 10 shows the measurement of red cell folate for samples of the stabilised whole blood preparation and fresh stored whole blood over a 50 day period;

FIGS. 12a, 12b, and 12c show the stability of the antigens CD3, CD4, CD8, and CD19, as measured by flow cytometry at 11 days post stabilisation;

FIGS. 16a, 16b, and 16c show the stability of the antigens CD3, CD4, CD8, and CD19, as measured by flow cytometry at 11 days post stabilisation;

DETAILED DESCRIPTION OF THE INVENTION

Figure 1A:
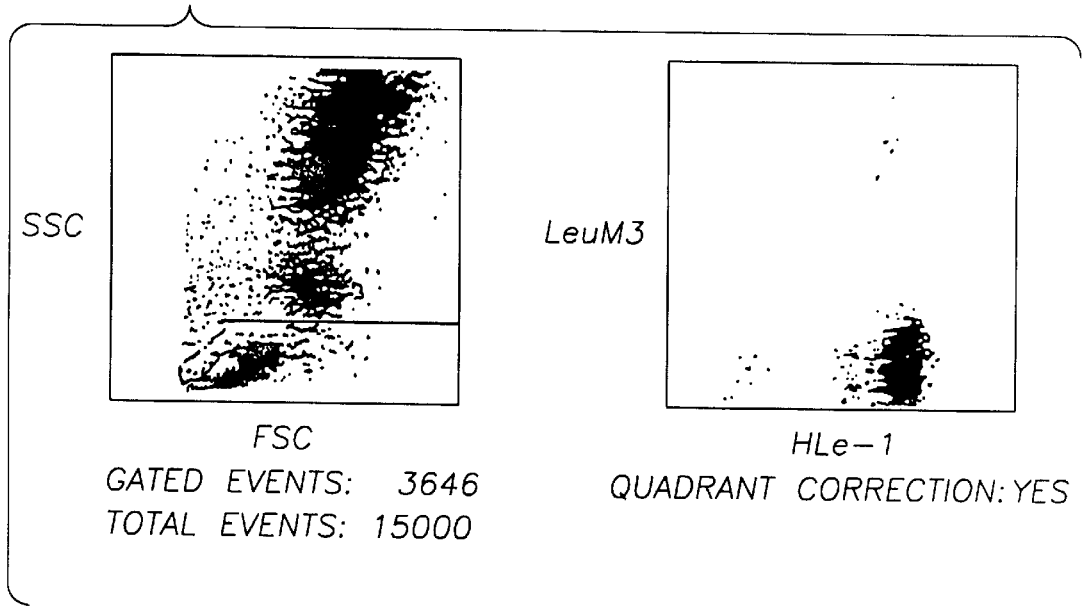
FIGS. 1a, 1b, 1c, and 1d show the flow cytometric characteristics of "fresh" blood after staining for the antigens CD3, CD4, CD8, and CD20.

In UK Patent Application No. GB2279653, leucocyte preparations separated from lysed whole blood are stabilised by the addition of a stabilising agent, and then added back to leucocyte depleted whole blood (red blood cells) to from a stabilised whole blood preparation. The present invention provides an alternative method for the preparation of stabilised whole blood in which the lysing and separating-steps can be omitted.

The invention will now be particularly described with reference to the manufacture of stabilised whole blood preparations for use in laboratory quality control procedures, although it will be appreciated that the invention is not limited thereto and that, for example, the stabilised whole blood preparations may find other uses, and that the stabilisation procedures described may find application in the manufacture of stabilised cell suspensions from sources other than blood, for example microbial cells, plant cells and similar materials derived from living tissue.

In this specification, a suspension of cells capable of lysis is defined as: a suspension of cells, such as, for example, whole human blood, in which specific cell populations can be selectively lysed using erythrocyte lysing reagents. Lysis comprises rupture of the cell membrane and leakage of the cell contents. Lysing reagents and conditions suitable for the selective lysis of the erythrocyte component of whole human blood include, for example, treatment in aqueous solution with an ammonium salt, for example, ammonium chloride, or a quaternary ammonium salt and urea, or a substituted urea, or urea derivative, as described in UK Patent Application No. GB92279653.

Whole blood preparations in this specification include preparations containing substantially all the components of fresh blood, and preparations containing substantially all the components of fresh blood other than plasma.

The process by which the stabilisation of the whole blood is achieved uses a series of stages incorporating the addition of both organic and inorganic compounds The initial process of drawing a unit of blood is well documented and can be any of those used by those employed in the art of venesection. Anticoagulated blood is preferably used, and several suitable anticoagulants are commercially available. However, the use of a potassium EDTA salt is preferred.

The process of stabilising the whole blood sample is usually performed within 24 hours of venesection but is preferably performed within 2 hours.

The fresh whole blood, containing an anticoagulant, is first centrifuged, and the plasma removed and retained.

The remaining cells are washed and then treated with an aged aqueous solution of a heavy metal compound, and particularly a heavy metal salt. Suitable heavy metals are those with complexing properties and having an atomic weight greater than 20, for example, aluminium, and transition metals such as chromium and manganese. Suitable metal compounds include inorganic acid salts, and particularly chlorides.

Particularly good results have been obtained using chromium compounds, such as, for example, chromic salts,for example, chromic chloride $CrCl_3$, and aluminium compounds, for example aluminium chloride $AlCl_3$.

The heavy metal compound can be dissolved in the appropriate concentration in an aqueous solution which is buffered to a pH of 6.5 to 7.5, preferably 6.7 to 7.4, more preferably around 7.2, and aged for a period of time sufficient to allow any precipitate to form. Suitable buffered aqueous solutions include, for example, phosphate buffered saline solutions.

Preferably, however, the heavy metal compound is stored as a relatively concentrated solution, for example, as a 1% w/v solution and is diluted to the desired concentration level with an appropriate aqueous buffer solution before use. With the preferred heavy metal compounds, it is found that the concentrated solutions are stable, but that on dilution precipitate may form as the pH rises. Sufficient time should be allowed for the solution to age and precipitation to occur before the solution is used.

The diluted aqueous solution of the heavy metal compound is therefore allowed to stand, preferably for at least one week, more preferably from one week to one month, before use. The reason why the performance of the solution improves with standing is at understood, but may be due to the formation of hydrated metal hydroxy ionic species in the solution. It has been observed with some buffered solutions of chromium compounds, for example, that the freshly made solutions change from green to purple over a 24 hour period, indicating the presence of charged complex ions, together with the formation of a precipitate which may be a chromium hydroxy polymeric species. This is preferably filtered off from the solution before use. The formation of a precipitate will, of course, lower the concentration of heavy metal ions in the solution, and if this should occur, an analysis of the solution should be carried out to determine whether the concentration of the heavy metal compound is still within the preferred range.

The aged solution of heavy metal compound retains its effectiveness over considerable periods of time, but is preferably discarded after 12 months and more preferably after 6 months.

The aqueous solution of the heavy metal compound is preferably added to the whole blood preparation as an isotonic solution in which the optimum final concentration of the heavy metal compound is preferably less than 1% w/v. more preferably from 0.005% to 0.75% w/v, still more preferably 0.01% to 0.5% w/v and most preferably from 0.05% to 0.25% w/v,. for example, 0.1% w/v. The pH of the aqueous solution is preferably from 6.5 to 7.5, preferably 6.7 to 7.4, before addition. The whole blood preparation is preferably exposed to the heavy metal compound for an incubation period of from 5 minutes to 18 hours, for example, about 60 minutes.

The incubation temperature is preferably from 0° C. to 8° C., more preferably from 2° C. to 60° C., for example about 4° C.

After the first incubation period, the whole blood is treated with an aqueous solution of paraformaldehyde, which can, for example, be at a preferred final concentration of up to 1% w/v, preferably from 0.1% to 0.5% w/v, for example 0.35% w/v. When making up the paraformaldehyde solution it is preferable to keep the temperature below 60° C., more preferably below 50° C., in order to avoid the reversion of paraformaldehyde to formaldehyde and evolution of formic acid. The age of the paraformaldehyde solution has also ben found to be important, and it is preferably greater than one week old, and no older than one month, preferably no older than two weeks.

In a preferred aspect of the invention, it has been found that very good results are obtained by mixing the paraformaldehyde, preferably in aqueous solution, with an aged aqueous solution of a heavy metal compound.

The aged aqueous solution of a heavy metal compound may be any of those previously described, and the metal compound may be present in the mixed solution in an amount of from 0.01% to 0.5% w/v. Preferably the ratio of heavy metal compound to paraformaldehyde in the solution is in the range of from 5:1 to 1:50, for example, around 1:3.5.

Preferably the aqueous paraformaldehyde solution has a pH of from 6.5 to 7.5, more preferably 6.7 to 7.4, and may comprise a suitable isotonic buffer. A preferred solution can be, for example, a 0.85% phosphate buffered saline solution.

A preferred mixed paraformaldehyde/heavy metal compound solution can be made, for example, by mixing a 0.7% w/v solution of paraformaldehyde with an equal volume of a 0.2% w/v solution of the heavy metal compound.

Exposure to the paraformaldehyde or mixed solution is preferably from 6 hours to 24 hours at a temperature range of from 0° to 8° C., preferably from 2° to 6° C., for example, about 4° C.

The interval between the sequential treatment stages 1) and 2) is preferably at least 30 minutes, more preferably at least one hour, still more preferably at least 12 hours, for example 24 hours.

After washing in isotonic phosphate buffered saline solution the plasma, if previously removed, can be added back to the stabilised whole blood preparation. This plasma can, but need not necessarily be, that obtained from the original donation. Bacterial growth inhibitors and antibiotics for example gentamycin are preferably also added to the final preparation. The preparation is then retained at between 0° C. and 8° C. for from 1 to 5 days before use.

All the above procedures are preferably carried out under sterile conditions and preferably the entire procedure is carried out in the venesection pack in which the donated blood is collected.

In the commercial manufacture of a stabilised whole blood preparation according to the invention, it is possible and may be preferable to pool a number of units of donated blood from different sources and to stabilise the resultant pool.

In another aspect of the invention, it is possible to add further cell lines to the whole blood preparation, either before or after the stabilisation of the whole blood preparation. For example, it is possible to add additional CD34+ cells in the form of cell line KG1 or as human umbilical cord blood (which is rich in CD34+ cells) to normal whole blood to provide a quality control for CD34+ cell measurements.

The stabilisation process can be applied to both normal and leukaemic cells providing a known normal control and an abnormal (leukaemic) control. It has been found that with normal cells, using chromium chloride as the metal compound usually provides the best results. However with leukaemic cells, aluminium chloride often gives the best results.

The invention provides a method of stabilising whole human blood preparations without the necessity to lyse the red blood cells (erythrocytes) and stabilise the leucocytes separately.

The stabilised whole blood preparations of the invention, can provide an excellent stable quality control and reference material, which can be used in leucocyte immunophenotyping by both UV microscopy and flow cytometry. The preparation is of value in the quality control of the whole blood lysing procedure without any excess contamination from debris. The stabilised sample can comprise all of the normal peripheral blood leucocytes (granulocytes, monocytes and lymphocytes) or subsets thereof. The procedure can, under optimum conditions, retain the leucocyte antigenic profiles ensuring phenotyping and quality control of the procedure. The values for the common antigenic determinants can be determined and can be stable for more than 300 days. The investigator can also successfully derive values for antigens that may be of specific interest. Furthermore, the preparation can be used to quality control the differential obtained from the flow cytometer. This is a parameter that is used for the monitoring of anti-viral therapy in HIV infected individuals.

New methods for phenotyping blood specimens are being developed which do not require the sample to be treated with a lysing agent after staining. These techniques are termed no-wash, no-lyse. The whole blood preparations of this invention can be used to provide quality control for these techniques and can also be used on flow cytometer that analyse no-wash, no-lyse procedures.

In general the stabilised whole blood preparations of the invention can be used in quality control of UV microscopy and flow cytometric immunophenotyping techniques, both of the whole blood lysis and whole blood non-lysis techniques, Investigations with preferred embodiments of the stabilised whole blood preparations of the invention show that they are also suitable for use in immunocytochemical analysis using techniques such as the alkaline phosphatase anti-alkaline phosphatase immunocytochemical technique (APAAP) and can for example be used to determine the antigenic profile of leucocytes on peripheral blood smears. They can be used as a day to day reference materials or in eternal (inter-laboratory) quality control. Multiple smears can be made in advance and then stored at −20° C. until use. The smears can be stained on a daily basis, or used as controls when staining other smears.

The stabilised whole blood preparations of the invention may also find application as standard reference materials for use in enzyme linked immunosorbent assay techniques (ELISA) and in immunoradiometric assay techniques.

Further uses of the stabilised whole blood preparations of the invention in the laboratory may include as a quality control and calibrant for haematology analyzers, as a quality control material for monitoring iron deficiency by the zinc protoporphyrin technique (ZPP), and as a quality control material in the red cell folate technique. Finally, on a broader basis, the stabilised whole blood preparations of the invention may find application in the quality control of blood glucose level tests, thereby enabling diabetic patients to carry out this technique in their own homes.

The invention is illustrated by the following Examples:

EXAMPLE 1

A stabilised whole blood preparation is made up as described below and its ageing characteristics compared with a similar untreated whole blood sample.

Preparation

1. Venesect a unit of 500 ml of blood into a sterile venesection pack containing 600 mg of ethylenediaminetetraacatic acid (disodium or tri potassium salt) dissolved in 50 ml of phosphate buffered saline solution (PBS).
2. Centrifuge the unit at 800 g for 1 hour. Remove and retain the plasma.
3. Wash the remaining cells twice with sterile phosphate buffered saline solution (PBS)
4. Remove the supernatant PBS.
5. Add 300 ml of filtered 0.1% aged (>1 month) Chromium Chloride hexahydrate (pH 6.7) in PBS and incubate for 1 hour in the dark at 4° C. mixing occasionally.
6. Centrifuge for 45 minutes at 800 g and decant supernatant.
7. Resuspend in 300 ml aged (>1 month) and filtered 0.1% Chromium Chloride hexahydrate pH 6.7 in 0.35% paraformaldehyde in PBS. Incubate at 4° C. in the dark for 16–22 hours.
8. Centrifuge at 800 g for 45 minutes and decant supernatant.
9. Wash twice by centrifuging at 800 g with PBS. Decant final supernatant.
10. Resuspend the stabilised whole blood in the plasma detailed in step 2. Add broad range antibiotics such as gentamycin, ciprofloxacin.
11. Place at 4° C. for 2–3 days until use.

Phosphate buffered Saline pH 7.2

7.83 g/l Sodium Chloride
0.36 g/l disodium EDTA
0.28 g/l Potassium Chloride
0.26 g/l Potassium dihydrogen phosphate (monobasic)
2.35 g/l disodium hydrogen phosphate (dibasic)

The comparative results are illustrated in the accompanying Drawings in which:

FIG. 1 shows the flow cytometric characteristics of "fresh" blood after staining for the antigens CD3, CD4, CD8, and CD20. The staining was carried out employing the whole blood lysis technique and the positive levels related to the negative controls (a) Forward & side scatter (FSC & SSC) characteristics, (b) CD3 PE & CD20 FITC, (c) CD3 FITC & CD4 PE, (d) CD3 FITC & CD8 PE.

FIG. 2 shows the effect of ageing on the flow cytometric FSC, and SSC of "fresh" unstabilized blood over a period of 8 days (a) Day 1, (b) Day 2 (c) Day 3, (d) Day 8.

Figure 1B:
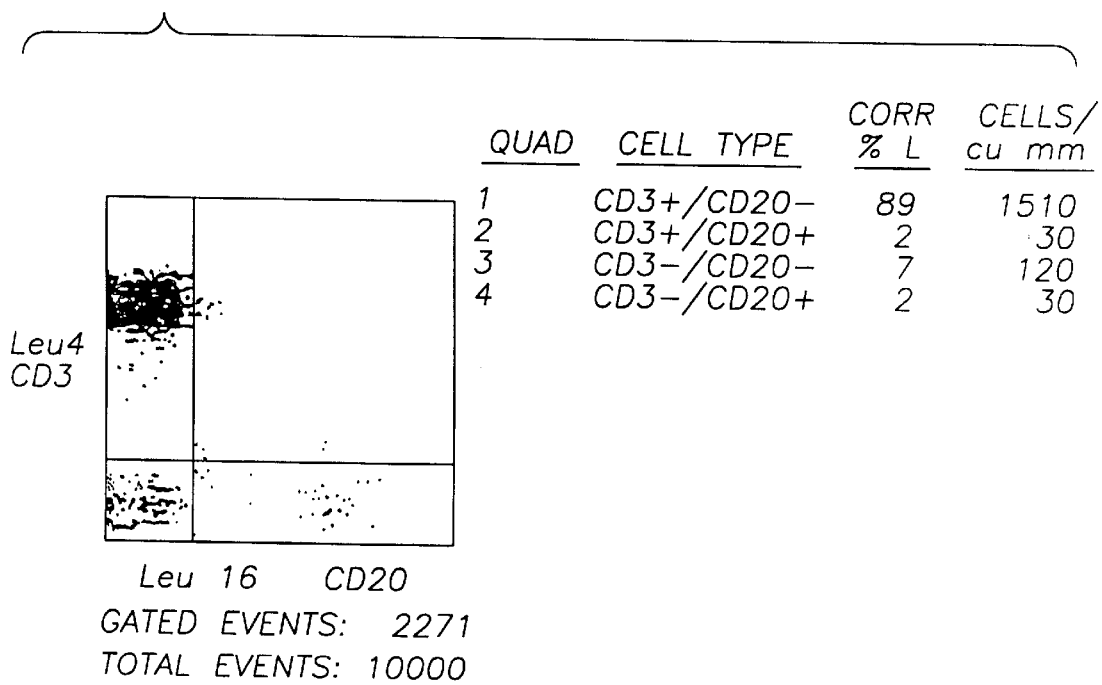
Figure 1C:
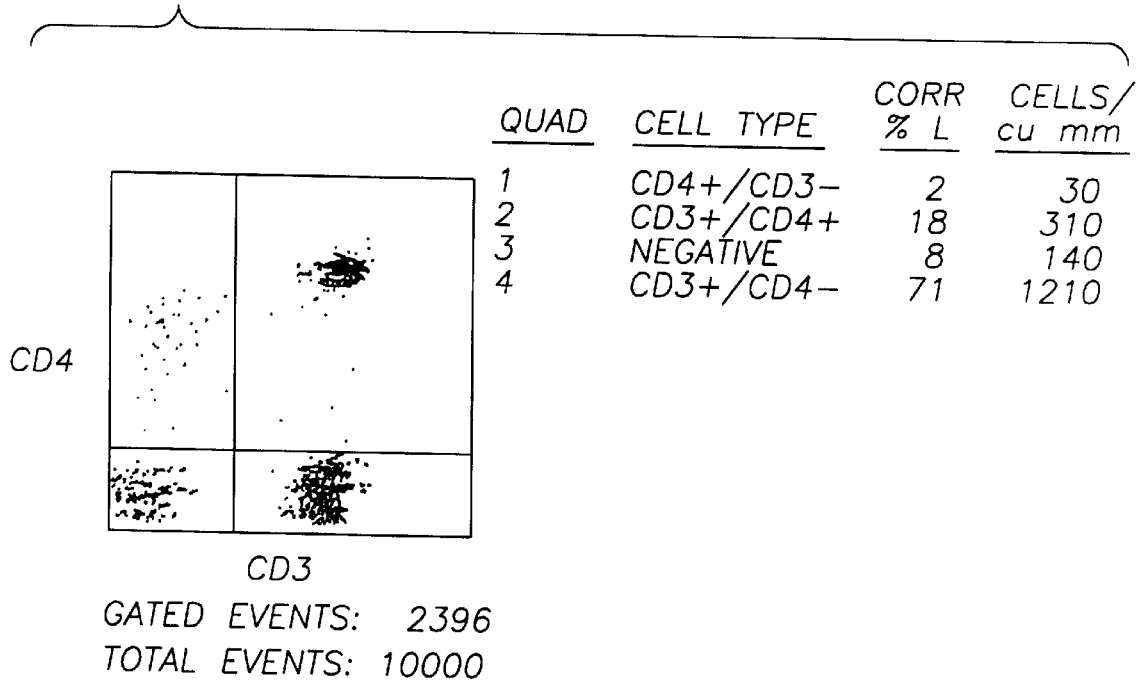
Figure 1D:
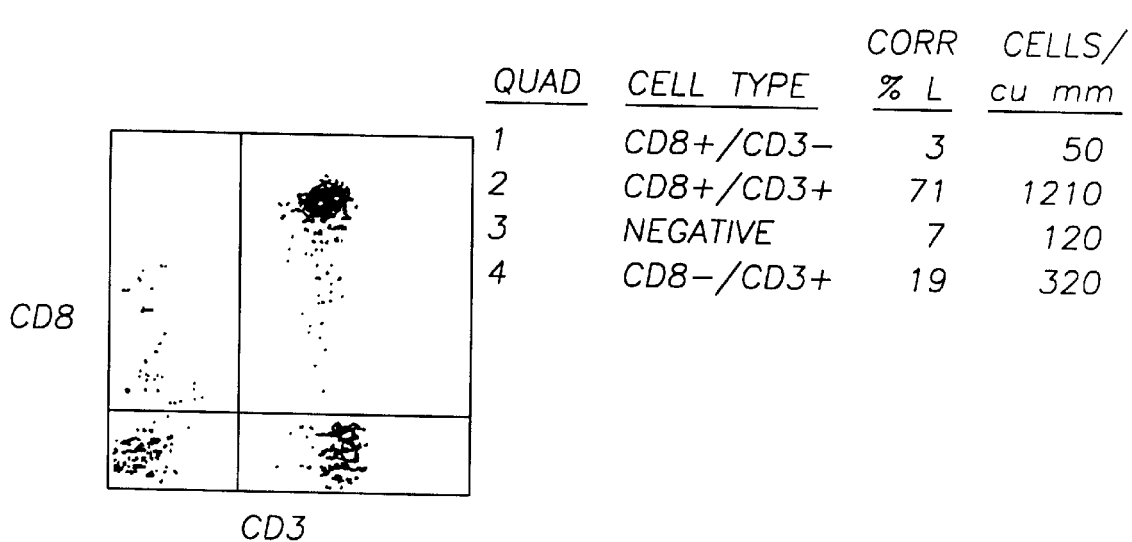
Figure 2A:
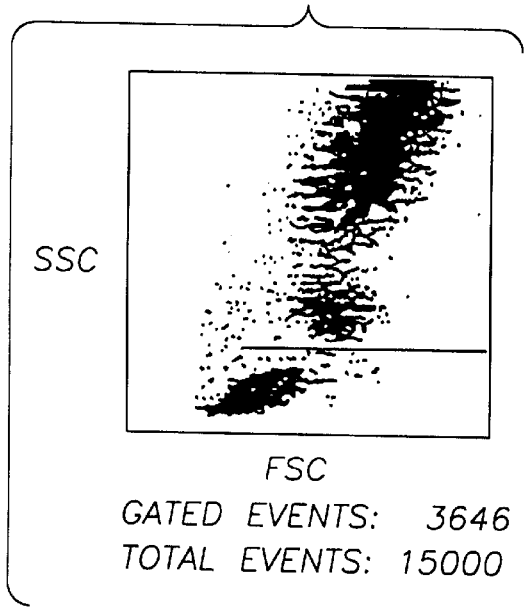
FIGS. 2a, 2b, 2c, and 2d show the effect of ageing on the flow cytometric FSC, and SSC of "fresh" unstabilised blood, over an 8 day period.
Figure 2B:
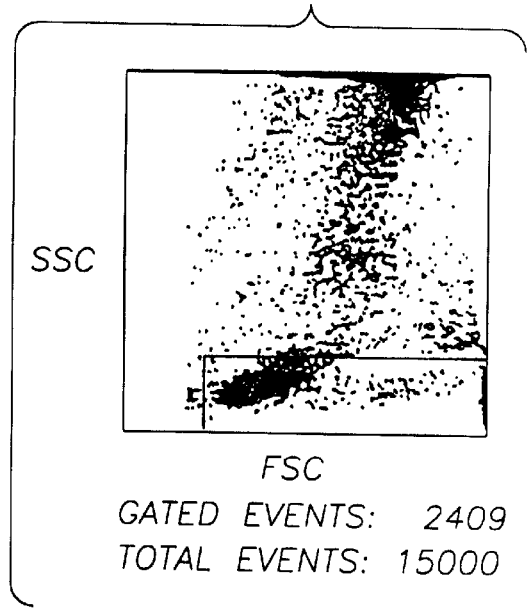
Figure 2C:
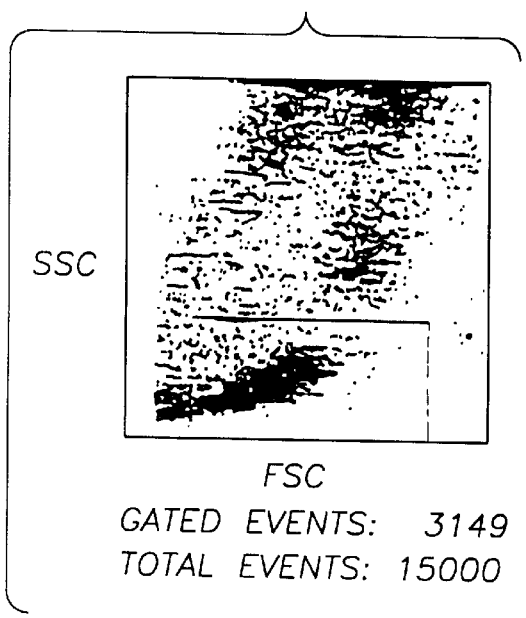
Figure 2D:
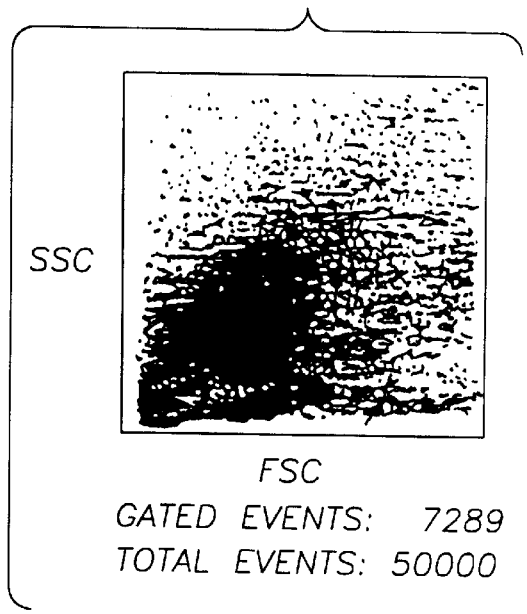
Figure 3A:
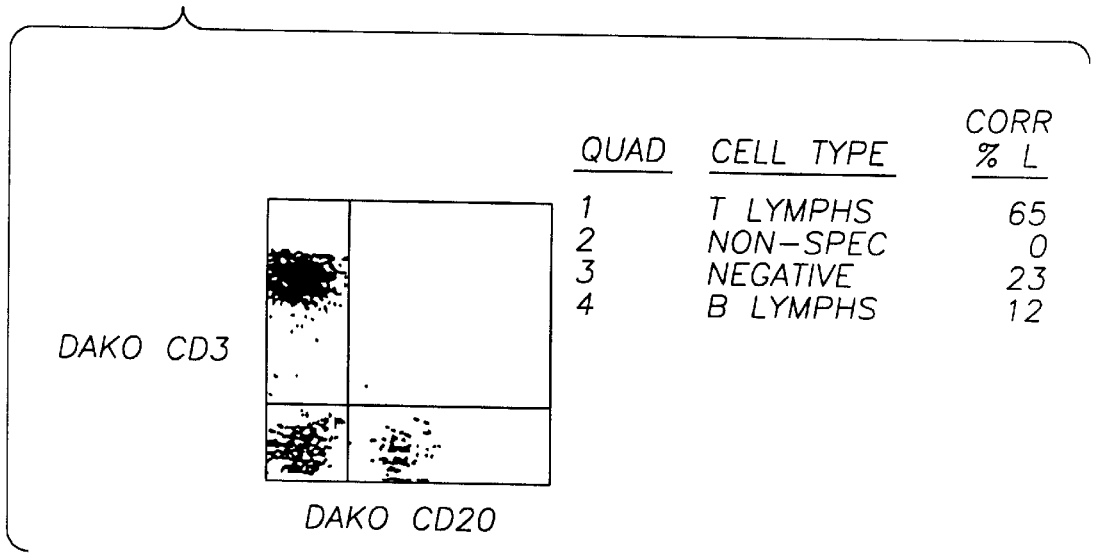
FIGS. 3a(i), 3b(i), 3a(ii), 3b(ii), 3a(iii), and 3b(iii) show the effect of ageing on the expression of antigens shown in FIGS. 1b, 1c, and 1d, over a 10 day period.
Figure 3B:
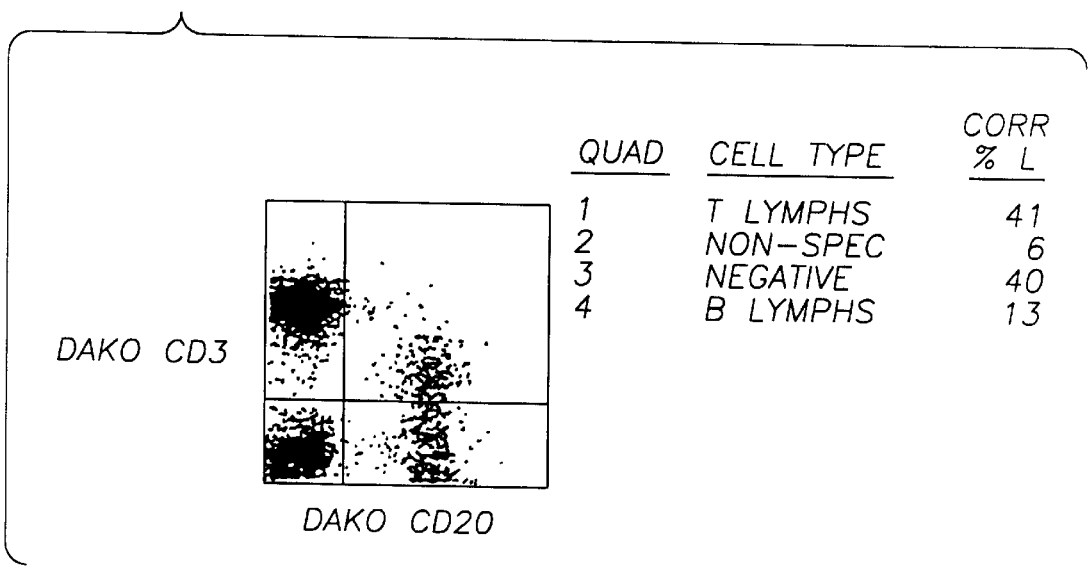

FIGS. 3a and 3b show the effect of ageing on the expression of the antigens described in FIG. 1b, c & d over a 10 day period 3a (i) (ii) (iii) Day 1, and 3b (i) (ii) (iii) Day 10.

Figure 4B:
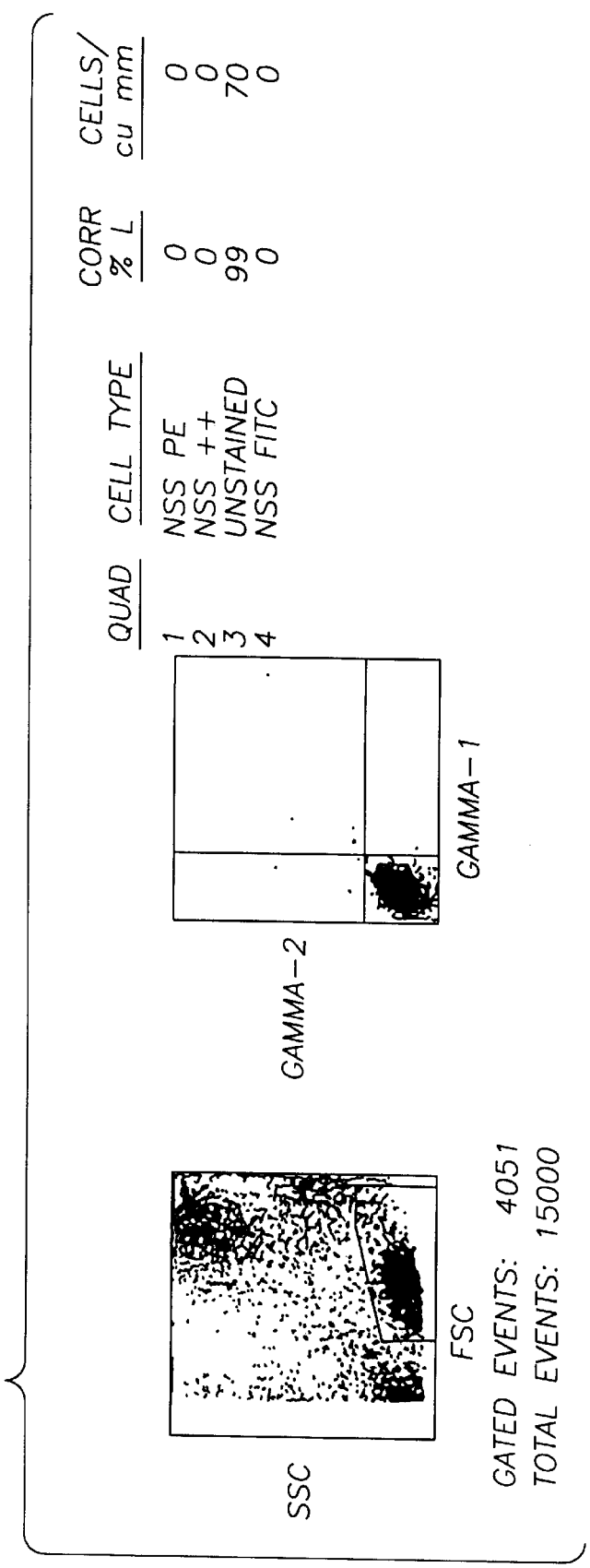

FIGS. 4a and 4b show the stability of FSC, SSC and the negative control characteristics, as determined by flow cytometry, upon the stabilised whole blood preparation over a period of 60 days, 4a day 3, 4b day 60.

Figure 5A:
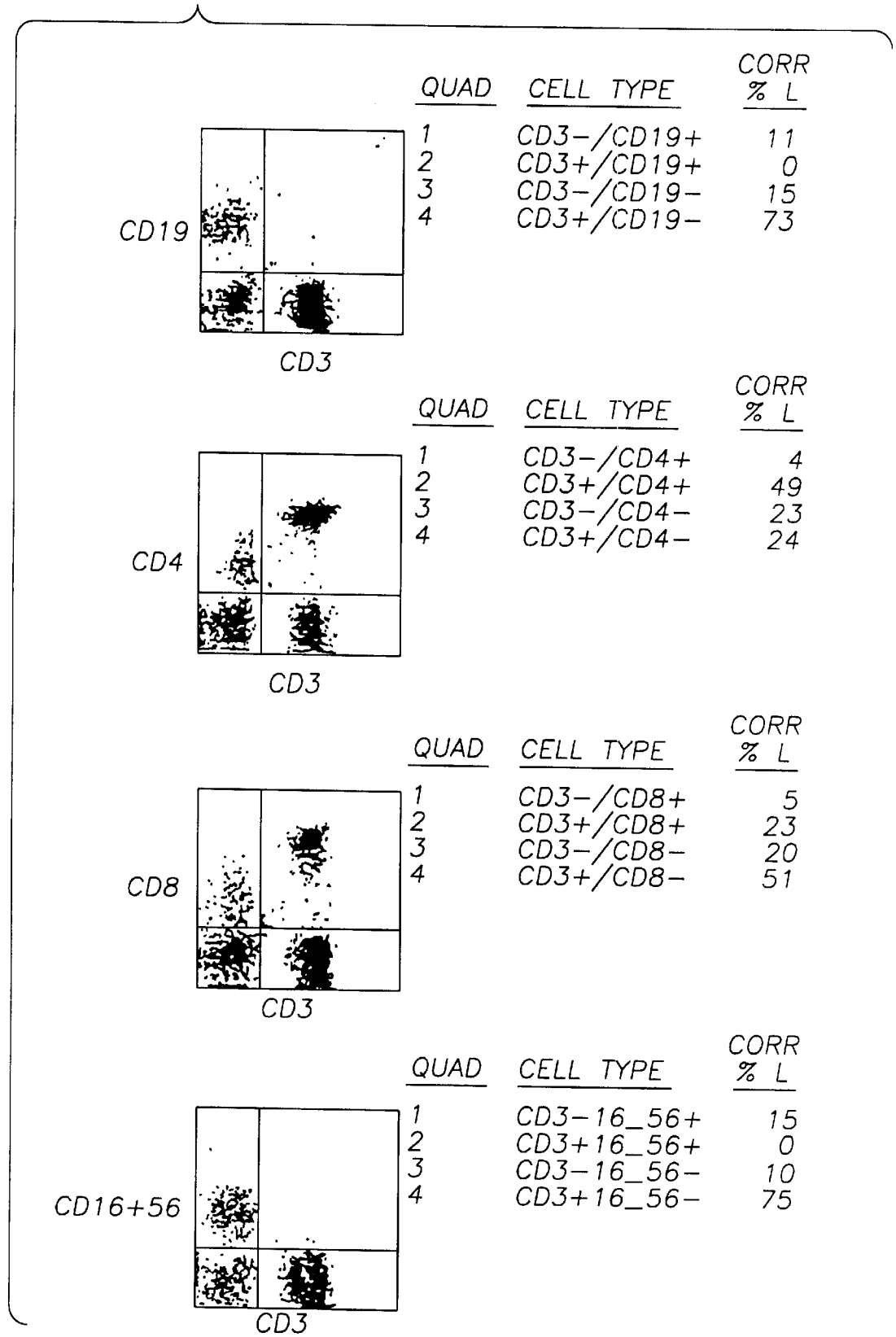
FIGS. 5a and 5b show the stability of various antigens as measured by flow cytometry.
Figure 5B:
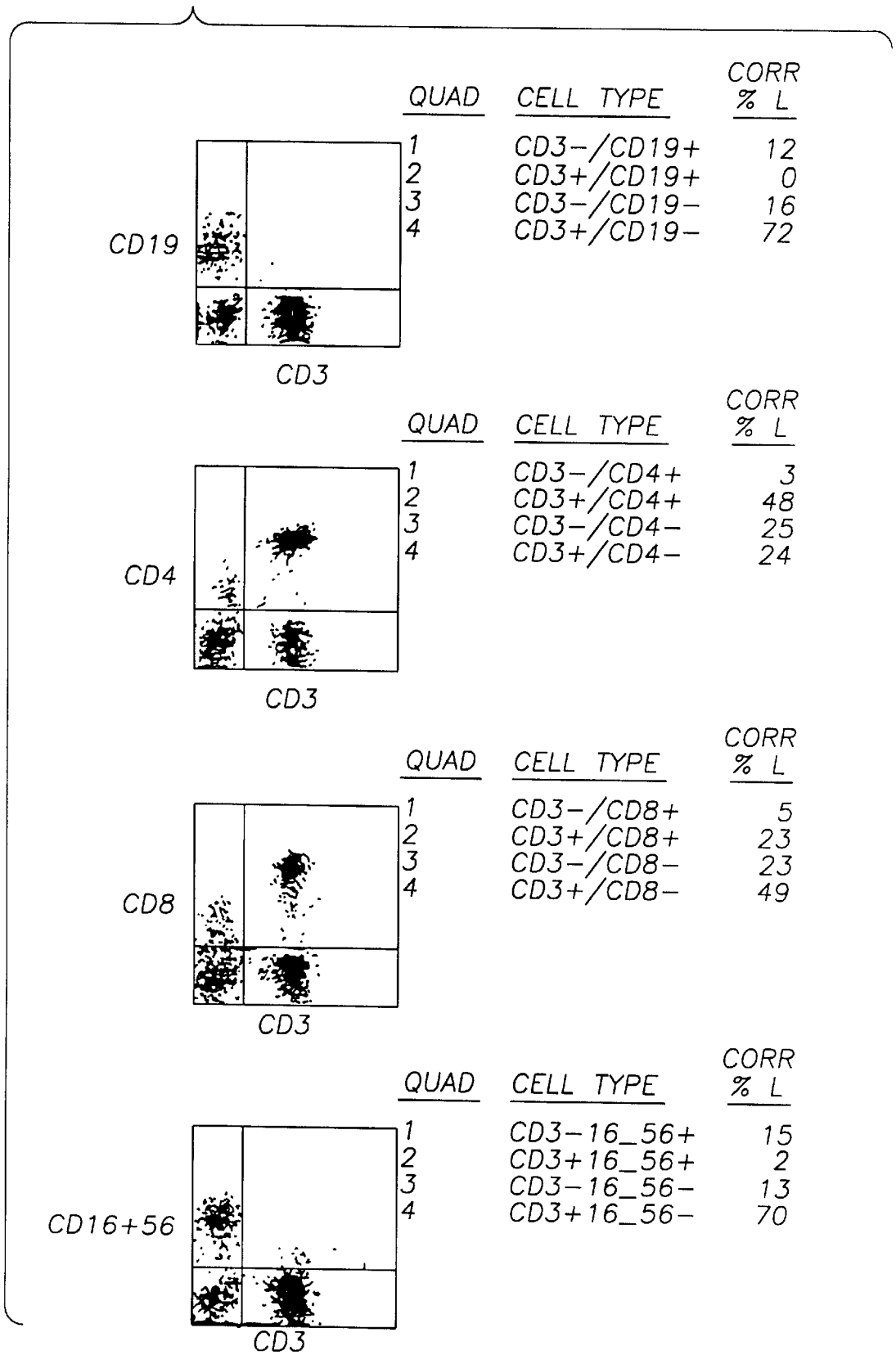

FIGS. 5a and 5b show the stability of the antigens CD3, CD4, CD8, CD19, and CD16+CD56, as measured by flow cytometry, over a 57 day period 5a Day 3, 5b Day 60.

Figure 6:
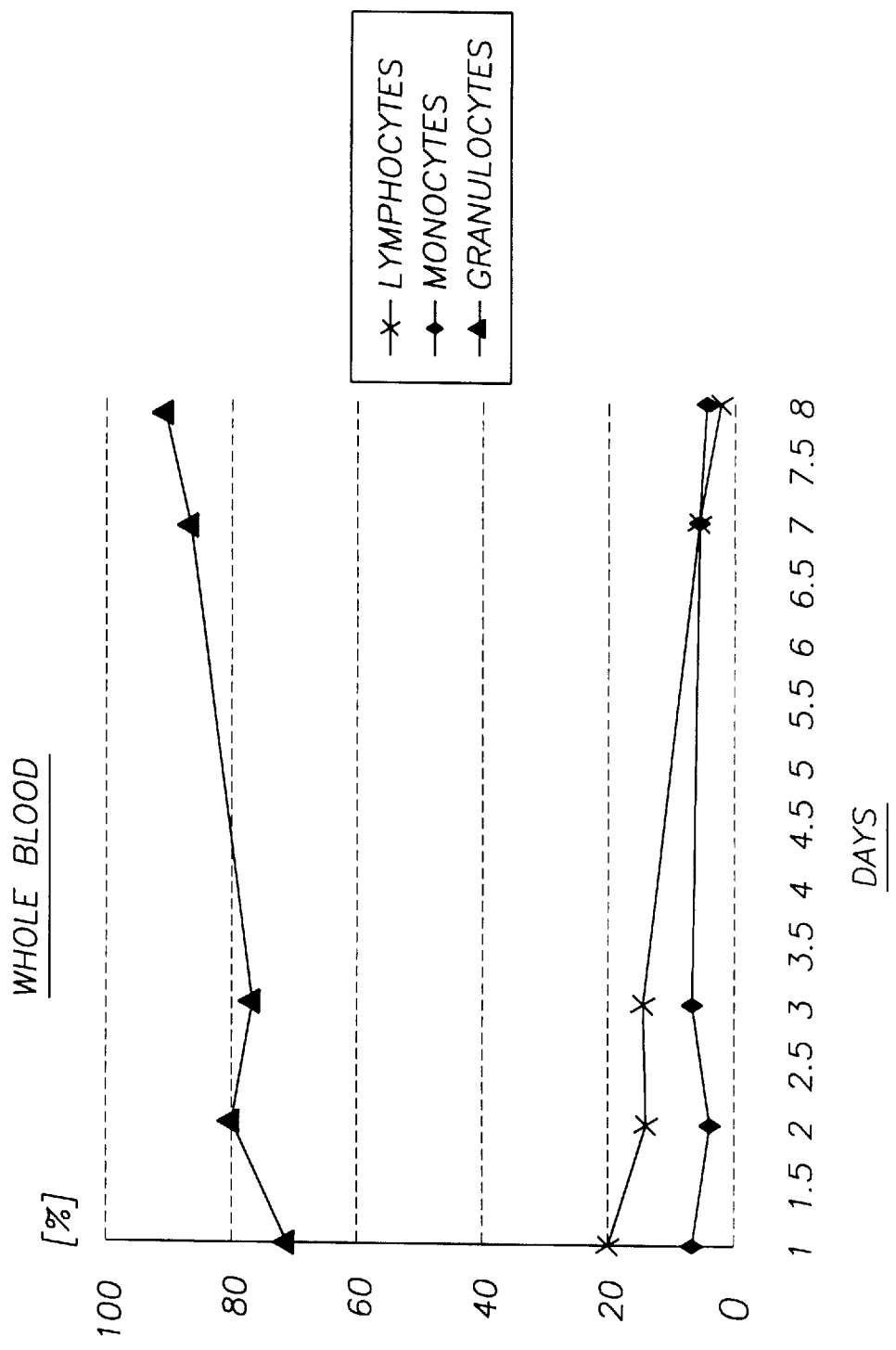
FIG. 6 shows the effect of storage on the flow cytometric leucocyte differential on "fresh" blood over an 8 day period.

FIG. 6 shows the effect of storage on the flow cytometric leucocyte differential on "fresh" blood over a period of 8 days. Further analysis after day 8 was not possible due to marked deterioration of the sample. Analysis used a FAC-Scan flow cytometer.

Figure 7:
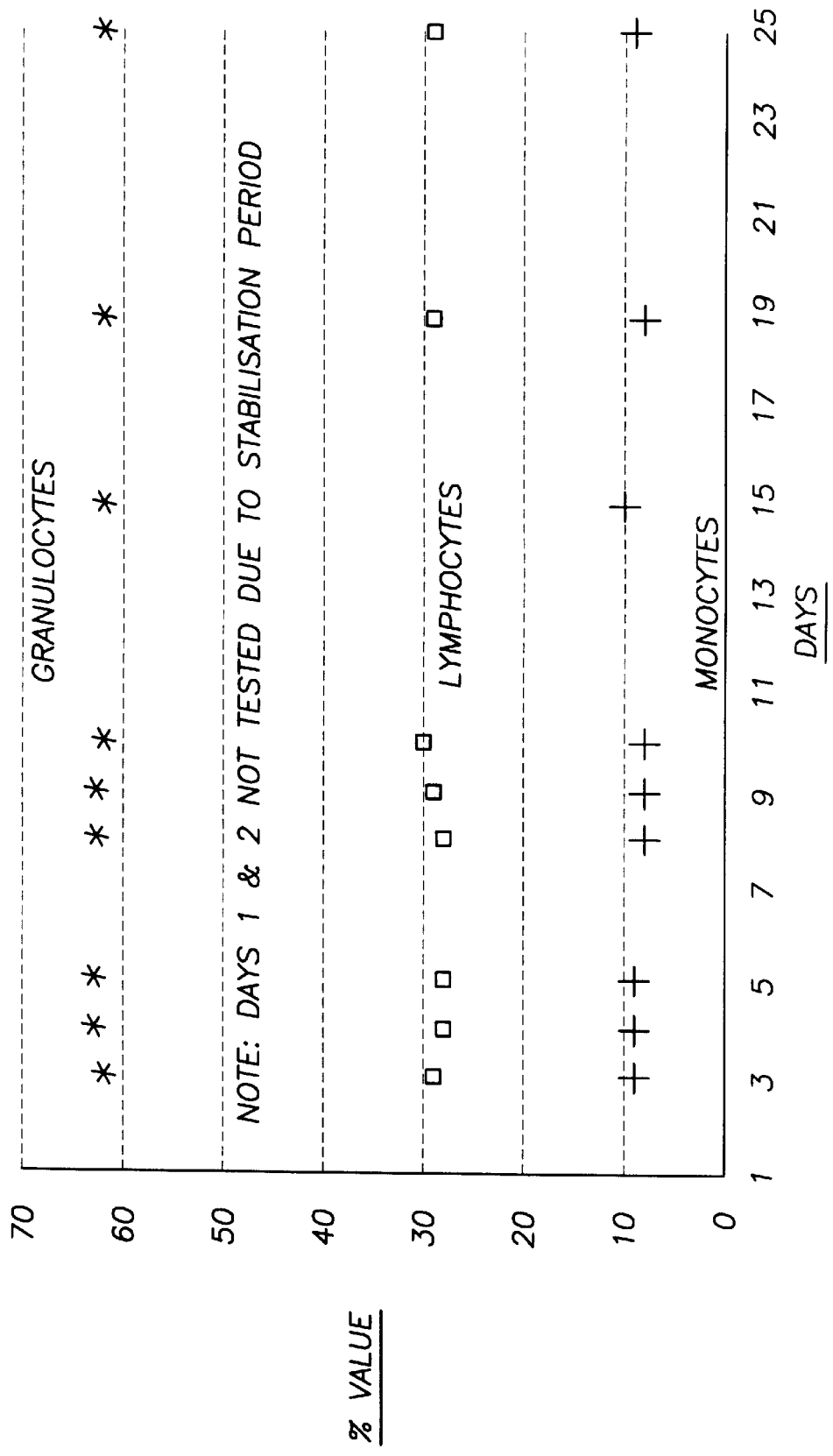
FIG. 7 shows the stability of the flow cytometric differential of the stabilised blood preparation over a 25 day period.

FIG. 7 shows the stability of the flow cytometric differential of the stabilised blood preparation over a 25 day period. Analysis used a FACScan (trademark) flow cytometer.

Figure 8:
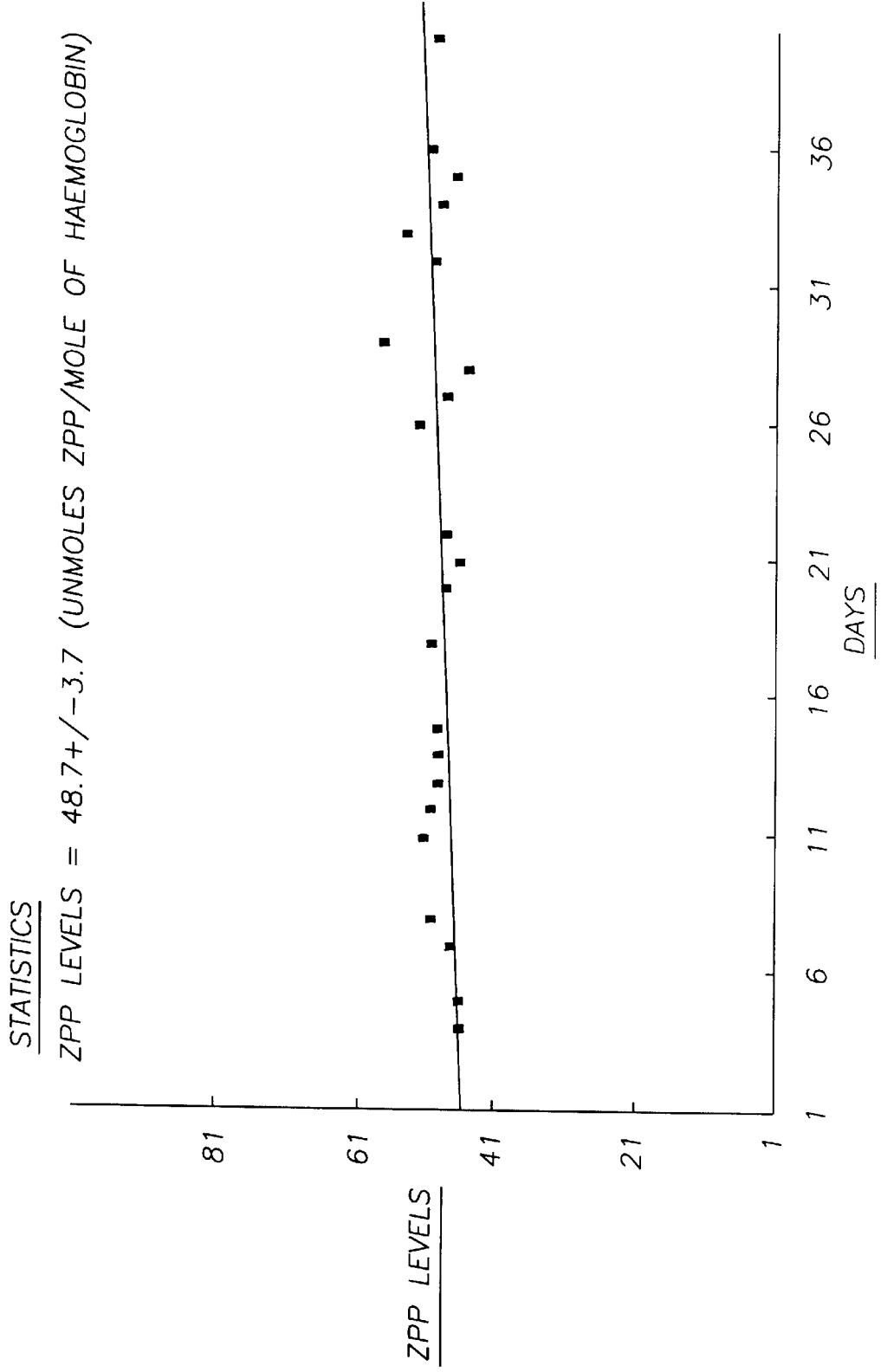
FIG. 8 shows the stability in zinc protoporphyrin (ZPP) level in a sample of the stabilised whole blood preparation over a 36 day period.

FIG. 8 shows the stability in zinc protoporphyrin (ZPP) level in a sample of the stabilised whole blood preparation over a period of 36 days measured in $\mu$moles ZPP/mole of haemoglobin.

Figure 9:
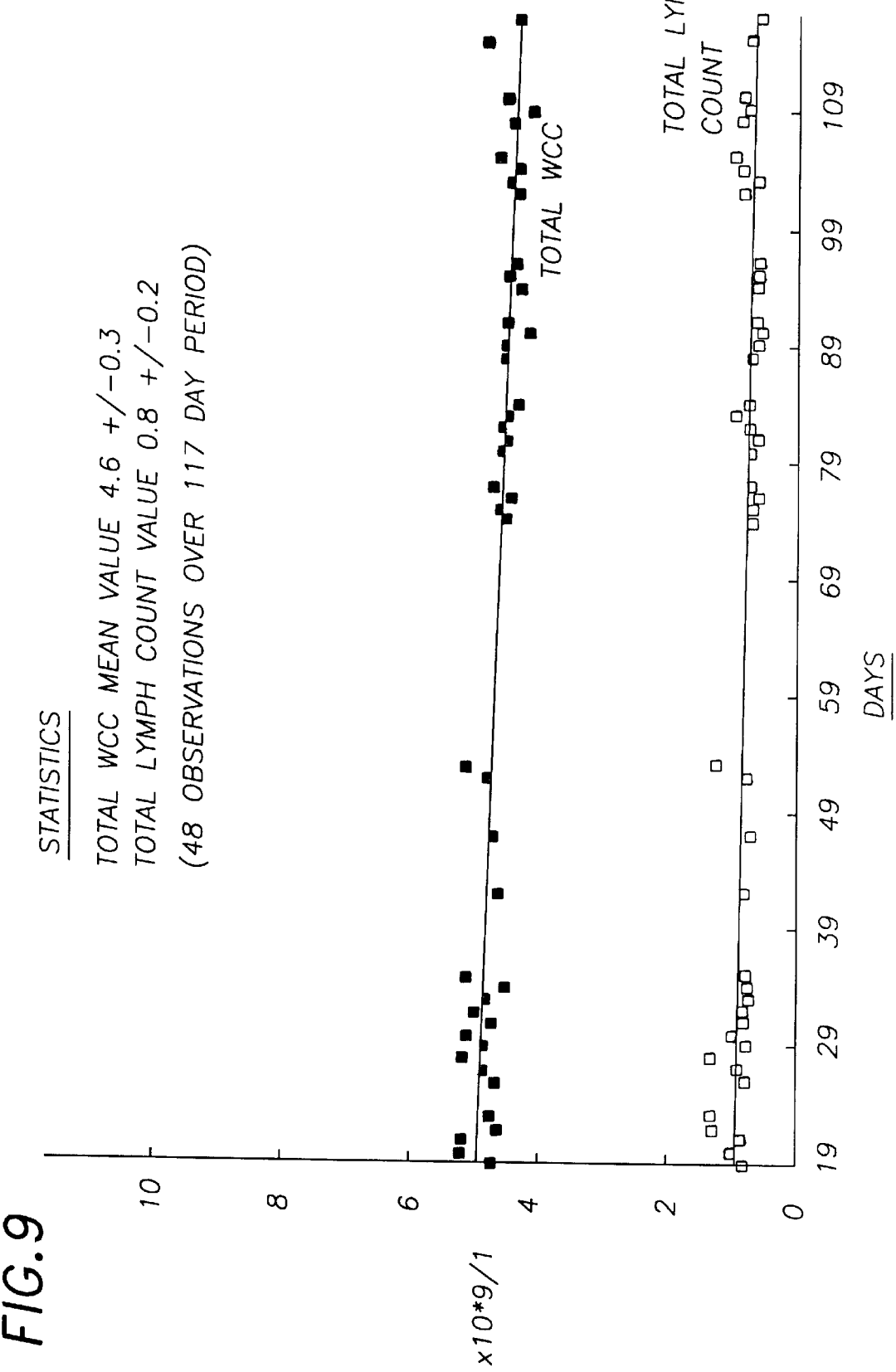
FIG. 9 shows the stability of the total white cell count and total lymphocyte count over a 117 day period for a sample of the stabilised whole blood preparations.

FIG. 9 shows the stability of the total white cell count and total lymphocyte count over a 117 day period for a sample of the stabilised whole blood preparations measured using a Toa (Sysmex) NE8000 (trademark) haematology analyser.

Finally, FIG. 10 shows the measurement of red cell folate for samples of the stabilised whole blood preparation and fresh stored whole blood over a 50-day period.

The flow Metric profile in FIG. 1 shows the normal position of the lymphocytes, monocytes and granulocytes after lysis of the red cells. The antigen staining characteristics are also shown in FIG. 1b, c, d, & e. As the sample increases with age (FIG. 2) the flow cytometric and antigen expression characteristics alter. At day 8 the amount of debris makes the analysis unsatisfactory. The fluorescence labelling characteristics have also deteriorated as shown by FIG. 3.

FIG. 4 displays the forward and side scatter characteristics together with the negative control of the stabilised sample at day 3 and day 60. The individual populations are retained in their respective positions immediately post stabilisation. After 60 days preservation the forward and side scatter flow cytometric characteristics remain intact (FIG. 4b). In addition the antigen expression characteristics remain unaltered over this period (FIG. 5). The same machine settings were retained throughout.

The stabilised blood preparation can be used to monitor the leucocyte differential. Using a specific combination of antibodies directed against the CD14 and CD45 antigens a three-population differential can be generated. FIG. 7 shows the stability of this parameter over 25 days, whereas FIG. 6 shows the instability of the "fresh" whole blood over an 8 day period. Analysis of the latter after this time was aborted due to contamination with excessive debris.

As shown in FIG. 8, ZPP levels in the stabilised whole blood preparation remain substantially constant, with only a very slight increase after 36 days. Similarly, as shown in FIG. 9, the total white cell count and total lymphocyte count are also scarcely affected by time over a 117 day period.

FIG. 10 shows the very substantial improvement obtained in the stability of red cell folate using a stabilised whole blood preparation according to the invention.

EXAMPLE 2

A stabilised whole blood preparation is made up as described in Example 1, except that the reactions with chromium chloride hexahydrate and with the mixture of chromium chloride hexahydrate and paraformaldehyde are carried out in phosphate buffered saline solution at a pH of 7.2.

Figure 11A:
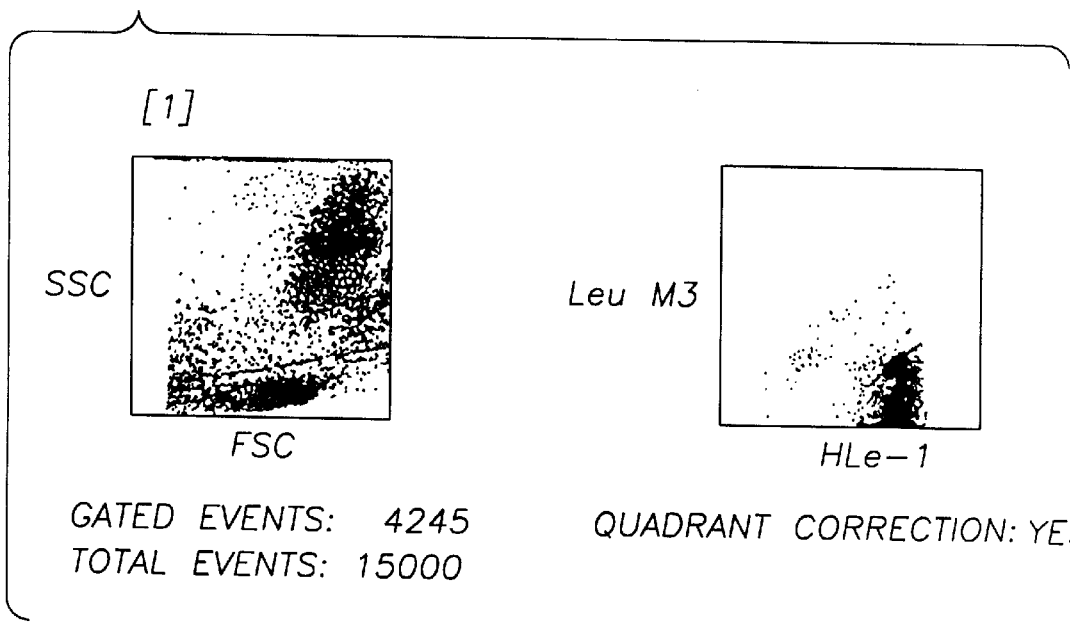
FIGS. 11a and 11b show the stability of the FSC, SSC and negative control characteristics, as determined by flow cytometry upon the stabilised whole blood preparation at 11 days post stabilisation.
Figure 11B:
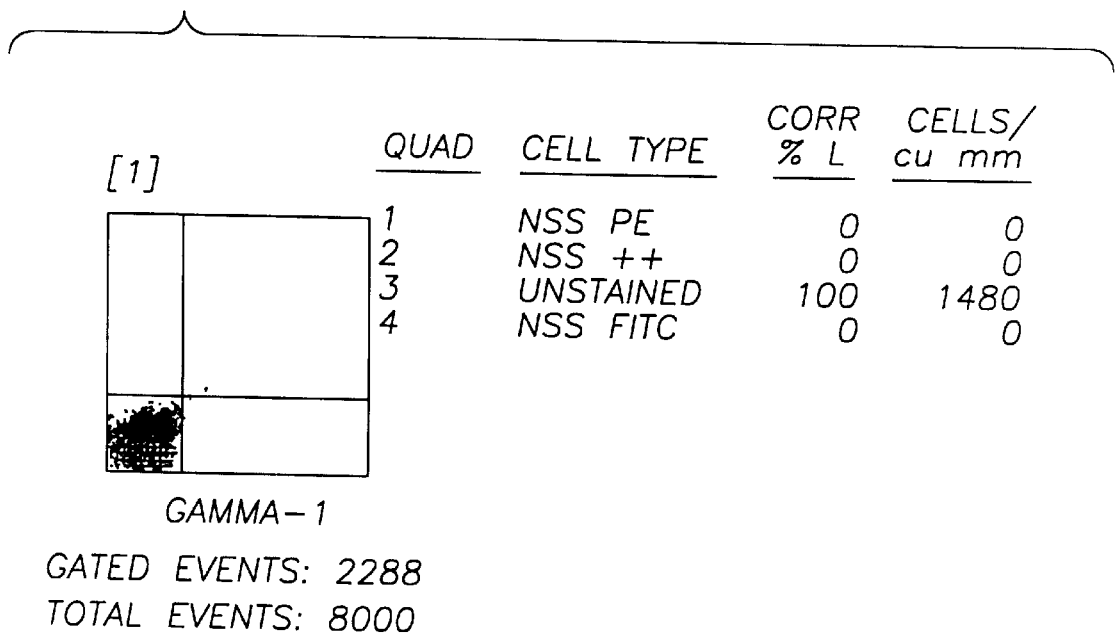

FIG. 11 shows the stability of the FSC, SSC (FIG. 11a) and negative control (FIG. 11b) characteristics, as determined by flow cytometry upon the stabilised whole blood preparation, at 11 days post stabilisation.

Figure 12C:
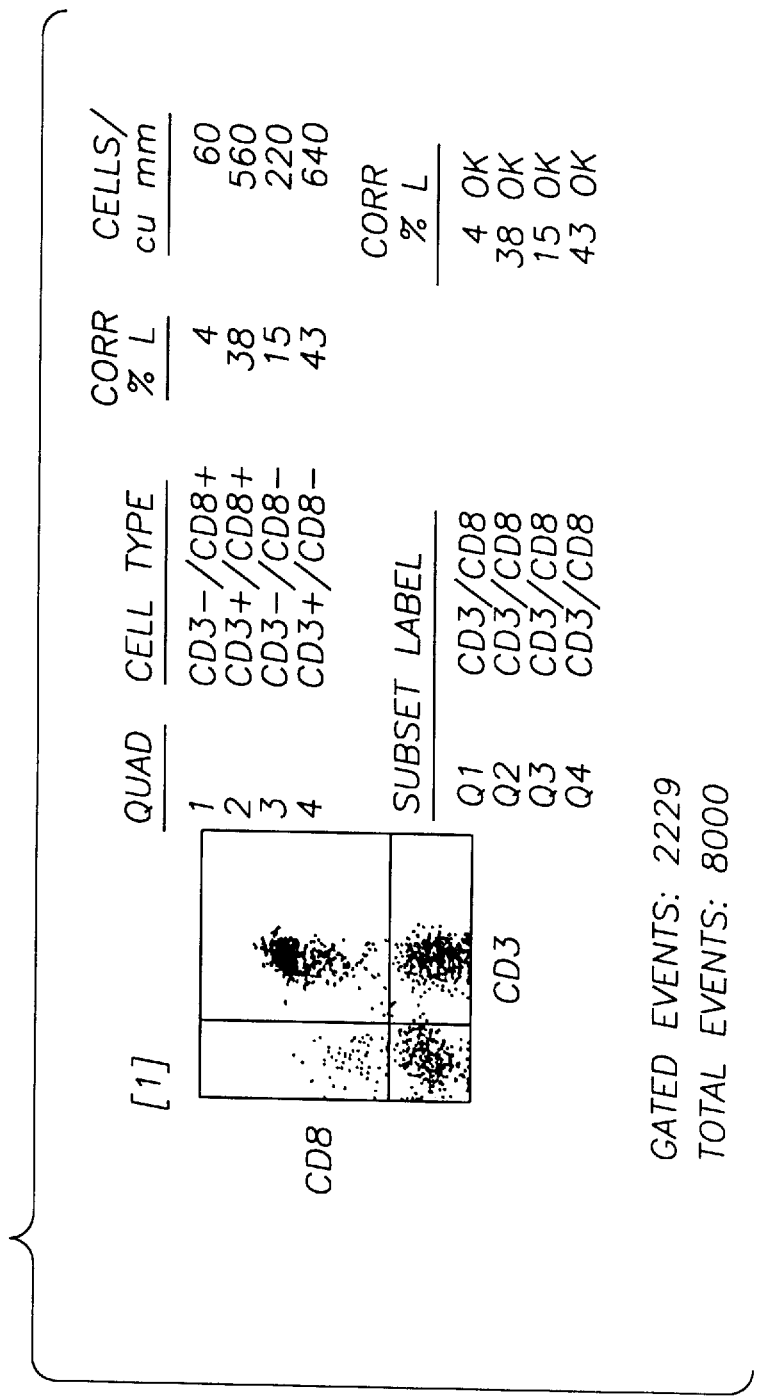

FIG. 12 (a), (b) and (c) shows the stability of the antigens CD3, CD4, CD8, and CD19 as measured by flow cytometry at 11 days post stabilisation.

Figure 13A:
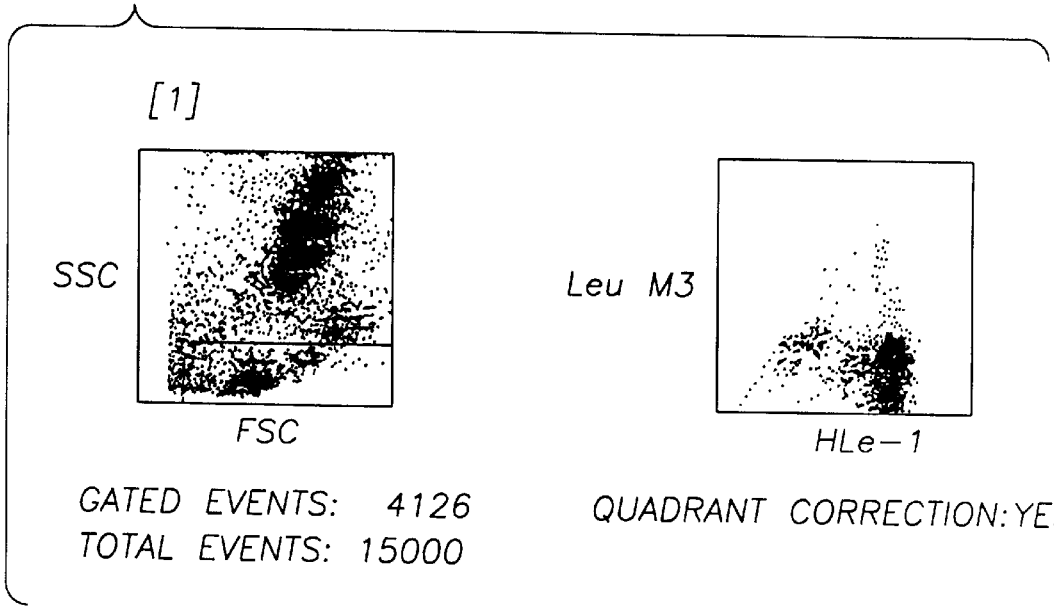
FIGS. 13a and 13b show the stability of the FSC, SSC and negative control characteristics as determined by flow cytometry, upon the stabilised whole blood preparation, at 29 days post stabilisation.
Figure 13B:
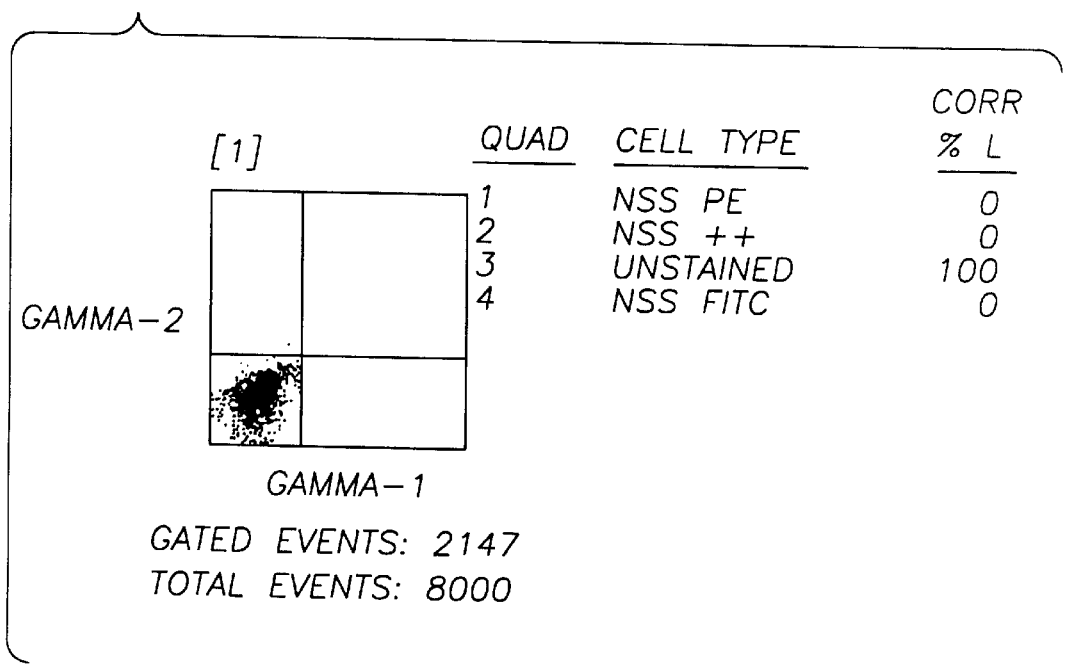

FIG. 13 (a) and (b) shows the stability of the FSC, SSC and negative control characteristics as determined by flow cytometry, upon the stabilised whole blood preparation, at 29 days post stabilisation.

Figure 14A:
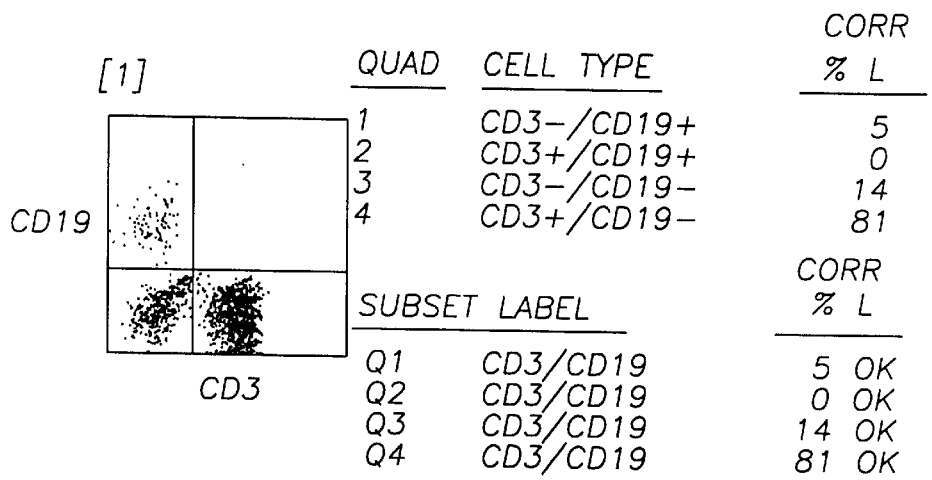
FIGS. 14a, 14b, and 14c show the stability of the antigens CD3, CD4, CD8, and CD19, as measured by flow cytometry at 29 days post stabilisation.
Figure 14B:
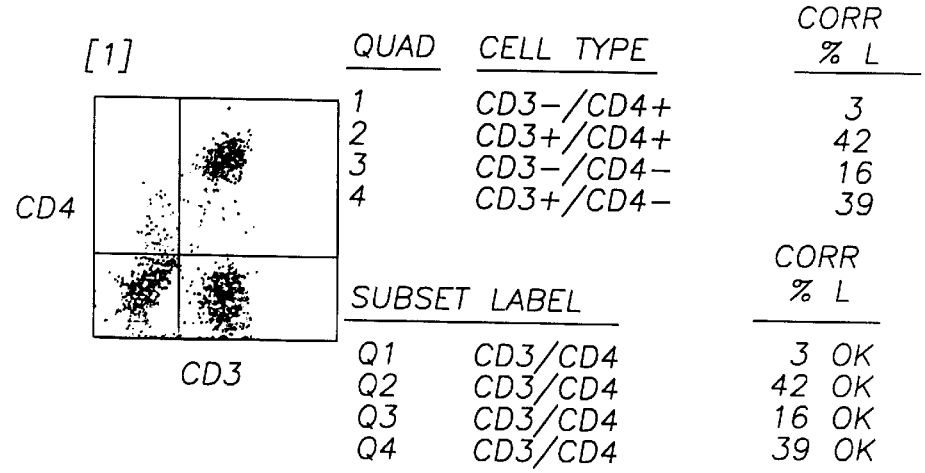
Figure 14C:
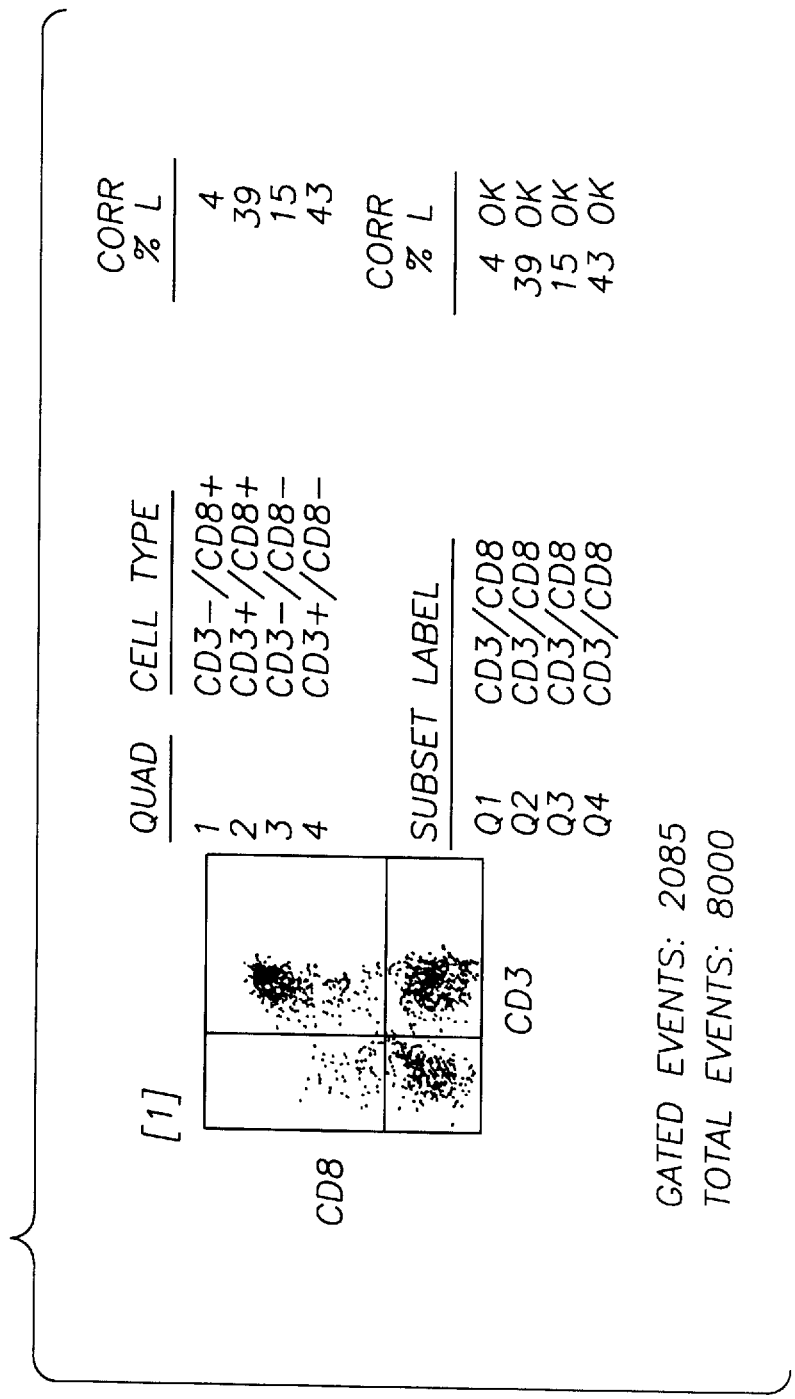

FIG. 14 (a), (b) and (c) shows the stability of the antigens CD3, CD4, CD8 and CD19 as measured by flow cytometry at 29 days post stabilisation.

EXAMPLE 3

A stabilised whole blood preparation is made up as described in Example 1, except that aluminium chloride hexahydrate is substituted for the chromium chloride hexahydrate, and the reactions with the aluminium chloride and the mixture of aluminium chloride and paraformaldehyde are carried out at pH 7.2.

Figure 15A:
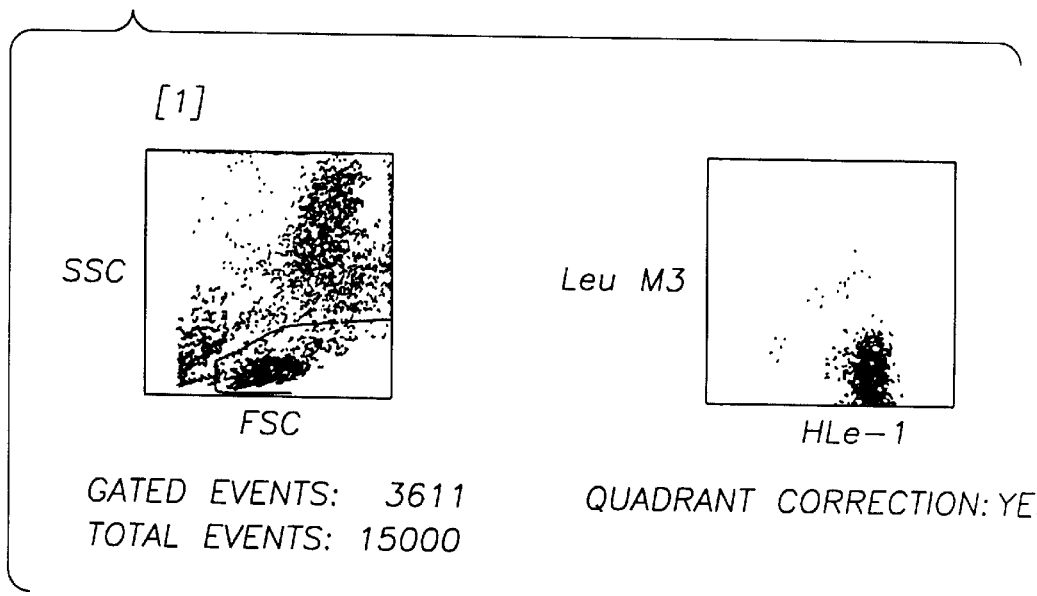
FIGS. 15a and 15b show the stability of FSC, SSC and negative control characteristics, as determined by flow cytometry upon the stabilised whole blood preparation at 11 days post stabilisation.
Figure 15B:
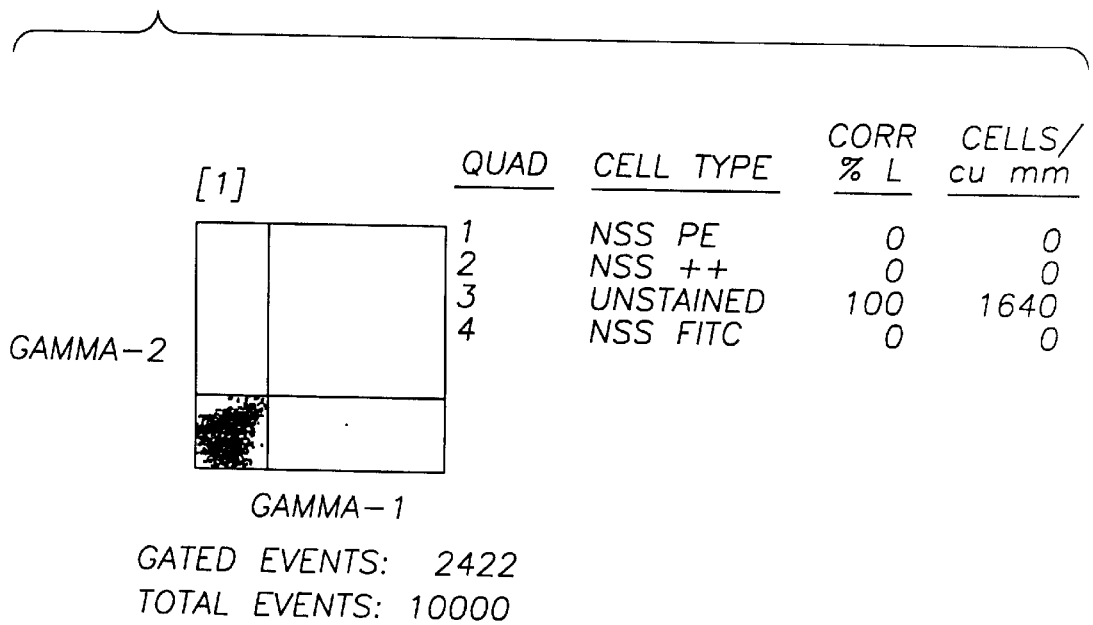

FIG. 15 (a) and (b) shows the stability of FSC, SSC and negative control characteristics, as determined by flow cytometry upon the stabilised whole blood preparation at 11 days post stabilisation.

Figure 16C:
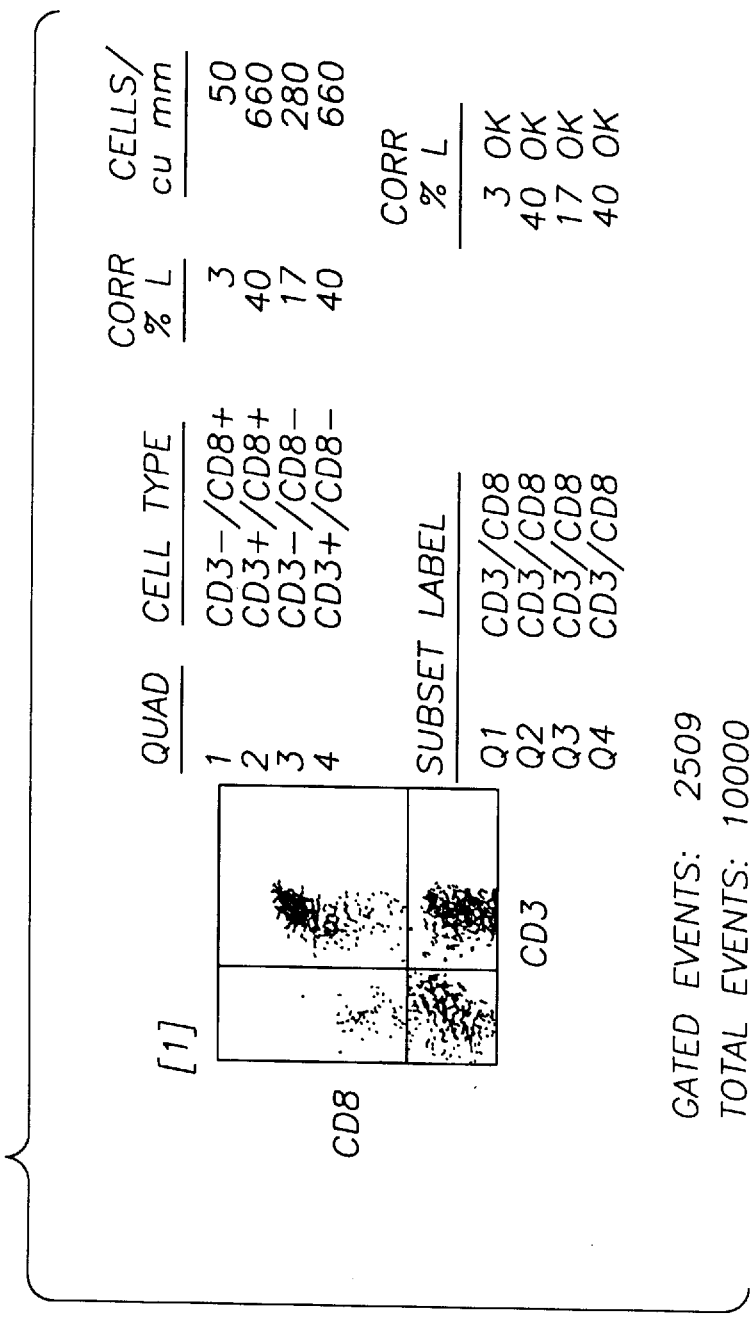

FIG. 16 (a), (b) and (c) show the stability of the antigens CD3, CD4, CD8 and CD19 as measured by flow cytometry at 11 days post stabilisation.

Figure 17A:
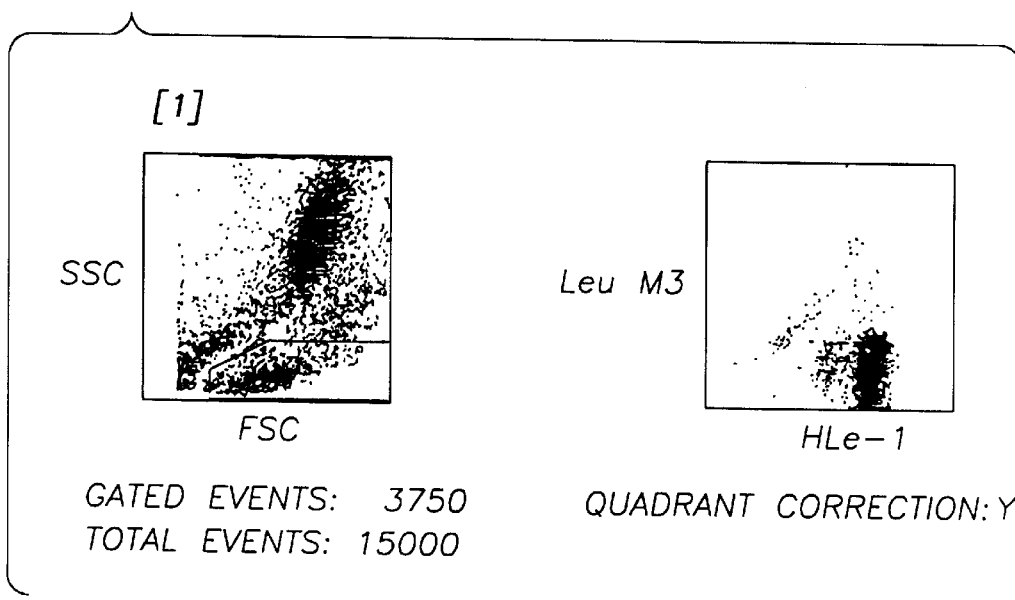
FIGS. 17a and 17b show the stability of FSC, SSC and negative control characteristics, as determined by flow cytometry upon the stabilised whole blood preparation at 29 days post stabilisation; and, FIGS. 18a, 18b, and 18c show the stability of the antigens CD3, CD4, CD8, and CD19, as determined by flow cytometry at 29 days post stabilisation.
Figure 17B:
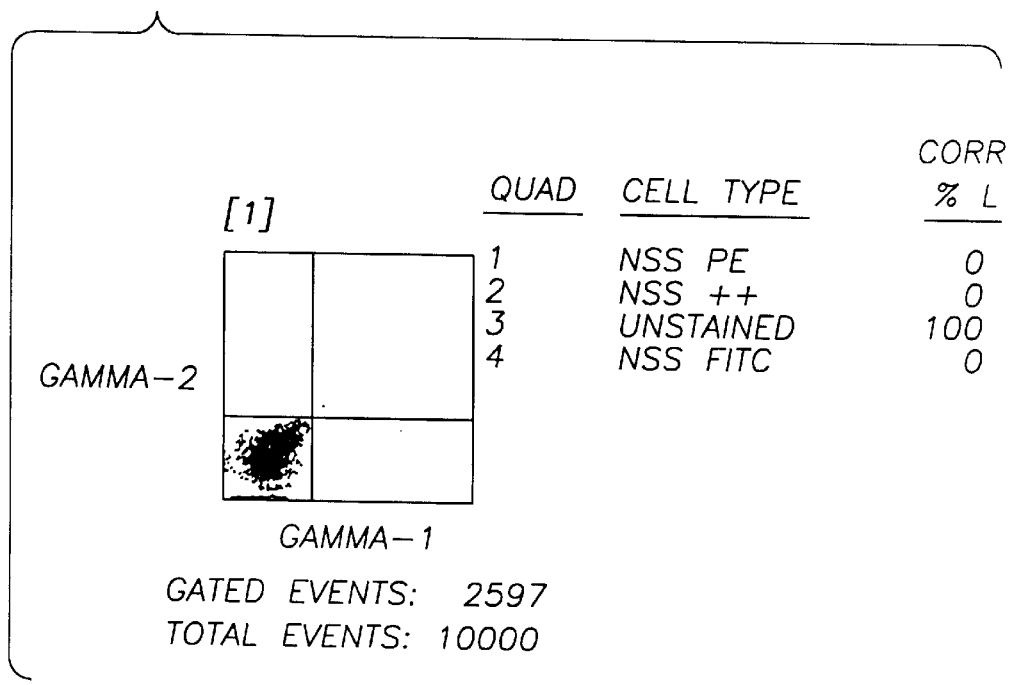

FIG. 17 (a) and (b) shows the stability of FSC, SSC and negative control characteristics as determined by flow cytometry upon the stabilised whole blood preparation at 29 days post stabilisation.

Figure 18A:
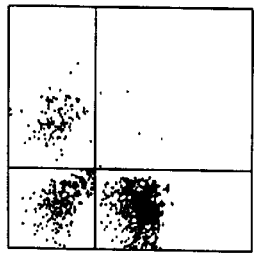
Figure 18B:
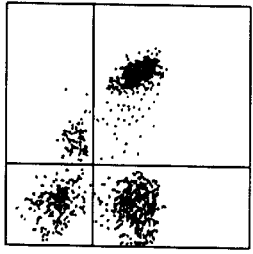
Figure 18C:
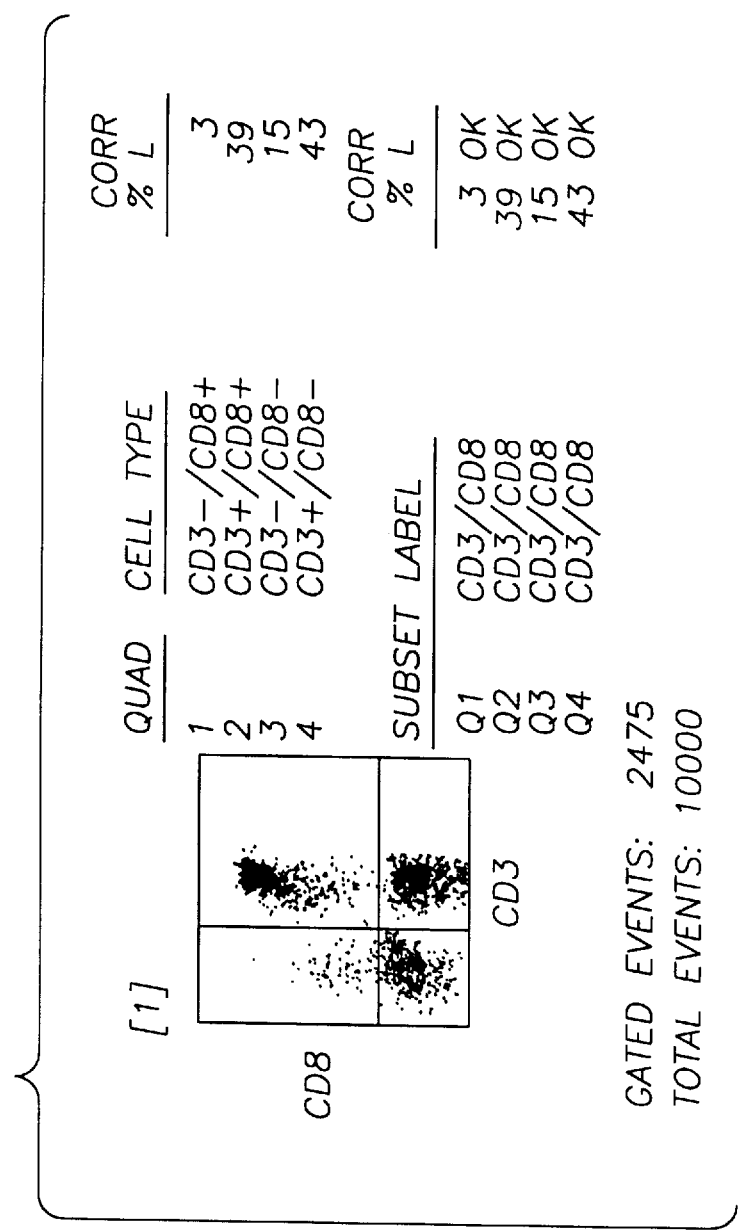

FIG. 18 (a), (b) and (c) shows the stability of the antigens CD3, CD4, CD8 and CD19 as determined by flow cytometry at 29 days post stabilisation.

The results show very good stabilisation of the whole blood preparation, with very little debris even after 29 days and good retention of antigenic characteristics.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract and drawings), and/or all of the steps or any method or process so disclosed, may be combined in any combination, except combinations where at least acme of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). This invention extends to any novel one, or any novel combination, of the features disclosed in this specification (including any accompanying claims, abstract and drawings), or to any novel one, or any novel combination, of the steps of any method or process so disclosed.

We claim:

1. A method of treating a suspension of cells capable of lysis comprising the steps of:
    preparing an aqueous solution of a heavy metal compound which has been aged at a pH of from 6.5 to 7.5 for at least 24 hours to allow precipitate to form;
    removing the precipitate from the solution to form an aged aqueous solution of the heavy metal compound, the aged aqueous solution comprising less than 1% weight per volume (w/v) of the heavy metal compound;
    mixing the cell suspension and the aged solution of the heavy metal compound at a pH of from 6.5 to 7.5 to form a first mixture; and,
    mixing the first mixture with a paraformaldehyde solution comprising up to 1% weight per volume (w/v) paraformaldehyde at a pH of from 6.5 to 7.5 to form a stabilised cell suspension which is still capable of lysis.

2. The method according to claim 1, in which the cell suspension is a whole blood preparation.

3. The method according to claim 1 or 2, in which the heavy metal is aluminium or a transition metal.

4. The method according to claim 1, in which the heavy metal compound is a metal salt.

5. The method according to claim 4, in which the metal salt is chromic chloride.

6. The method according to claim 4, in which the metal salt is aluminum chloride.

7. The method according to claim 1, in which the aqueous solution of a heavy metal compound has a pH of from 6.7 to 7.4.

8. The method according to claim 1, wherein the step of preparing the aqueous solution of the heavy metal compound further comprises the step of forming the aqueous solution of the heavy metal compound by diluting a relatively concentrated solution of the heavy metal compound and raising its pH from 6.5 to 7.5 by the addition of an aqueous buffer solution.

9. The method according to claim 1, in which the aqueous solution of a heavy metal compound is aged for at least one week before use.

10. The method according to claim 1, in which the aqueous solution of the heavy metal compound is added to the cell suspension as a 0.01% to 0.5% w/v solution.

11. The method according to claim 1, in which the cells are exposed to the aqueous solution of the heavy metal compound for a period of from 5 minutes to 18 hours at a temperature of from 0° C. to 8° C.

12. The method according to claim 1, in which the paraformaldehyde is added as a 0.1% to 0.5% w/v aqueous solution.

13. The method according claim 1, in which the paraformaldehyde solution is aqueous and has a pH of from 6.7 to 7.4.

14. The method according to claim 1, wherein in the step of mixing the first mixture with the paraformaldehyde solution, the paraformaldehyde solution further comprises an additional amount of an aged solution of a heavy metal compound having a pH in the range of from 6.5 to 7.5.

15. The method according to claim 14, in which the ratio of heavy metal compound in the additional amount of the aged solution of the heavy metal compound to paraformaldehyde in the solution is in the range of from 5:1 to 1:50.

16. The method according to claim 1, wherein in the step of mixing the first mixture with the paraformaldehyde solution, the exposure of the cell suspension of the first mixture to the paraformaldehyde solution is for a time period from 6 to 24 hours at a temperature of from 0° C. to 8° C.

17. The method according to claim 1, in which the steps are carried out sequentially at a time interval of from 1 hour to 24 hours.

18. The method according to claim 1, in which a further cell line is added to a whole blood preparation, either before or after the stabilisation of the whole blood preparation.

19. The method according to claim 18, in which the cell line comprises CD34+ cells.

20. A stabilised cell suspension capable of lysis prepared by a method according to claim 1.

21. The method of claim 1 wherein the paraformaldehyde solution further comprises an additional amount of an aged solution of a heavy metal compound.

22. A method of treating a suspension of cells capable of lysis comprising the steps of:

preparing a 0.1%–0.5% aqueous solution of a heavy metal compound which has been aged at pH 6.5 to 7.5 for at least one week, which is an amount of time sufficient to allow any precipitate to form;

removing the precipitate from the solution to form an aged aqueous solution of the heavy metal compound;

mixing the cell suspension and the aged solution of the heavy metal compound at pH 6.5 to 7.5 and at a temperature of 0° C. to 8° C. to form a first mixture; and, mixing the first mixture with a solution comprising 0.1%–0.5% paraformaldehyde at a pH of 6.5 to 7.5 and at a temperature of 0° C. to 8° C. to form a stabilized cell suspension which is still capable of lysis.

23. The method of claim 22 wherein the paraformaldehyde solution further comprises the aged solution of a heavy metal compound.

* * * * *